US008927223B2

(12) United States Patent
Robertson et al.

(10) Patent No.: US 8,927,223 B2
(45) Date of Patent: Jan. 6, 2015

(54) IMMUNOASSAY METHODS

(71) Applicant: OncImmune Ltd., Nottingham (GB)

(72) Inventors: John F. R. Robertson, Nottingham (GB); Andrea Murray, Leicestershire (GB); Caroline Chapman, Leicestershire (GB); Anthony Barnes, Dunwoody, GA (US)

(73) Assignee: OncImmune Ltd., Nottingham (GB)

(*) Notice: Subject to any disclaimer, the term of this patent is extended or adjusted under 35 U.S.C. 154(b) by 0 days.

(21) Appl. No.: 14/035,092

(22) Filed: Sep. 24, 2013

(65) Prior Publication Data

US 2014/0038212 A1    Feb. 6, 2014

Related U.S. Application Data

(62) Division of application No. 11/854,050, filed on Sep. 12, 2007, now Pat. No. 8,574,848.

(60) Provisional application No. 60/844,158, filed on Sep. 13, 2006.

(51) Int. Cl.
G01N 33/53    (2006.01)
G01N 33/574   (2006.01)
G01N 33/543   (2006.01)
G01N 33/564   (2006.01)

(52) U.S. Cl.
CPC .... *G01N 33/57484* (2013.01); *G01N 33/54393* (2013.01); *G01N 33/564* (2013.01); *G01N 2800/52* (2013.01)
USPC .............................................. 435/7.1; 435/7.2

(58) Field of Classification Search
None
See application file for complete search history.

(56) References Cited

U.S. PATENT DOCUMENTS

| | | | |
|---|---|---|---|
| 4,241,044 A | 12/1980 | Kim | |
| 4,898,951 A | 2/1990 | Symons | |
| 4,937,185 A | 6/1990 | Webb et al. | |
| 5,110,911 A | 5/1992 | Samuel et al. | |
| 5,157,020 A | 10/1992 | Kay et al. | |
| 5,501,955 A | 3/1996 | Bergman | |
| 5,561,049 A | 10/1996 | Vold et al. | |
| 5,652,115 A | 7/1997 | Marks et al. | |
| 5,721,105 A | 2/1998 | Bergmann | |
| 5,726,023 A | 3/1998 | Cheever et al. | |
| 5,747,268 A | 5/1998 | Herring et al. | |
| 5,763,164 A | 6/1998 | Calenoff | |
| 5,827,666 A | 10/1998 | Finn et al. | |
| 5,876,728 A | 3/1999 | Kass et al. | |
| 5,885,793 A | 3/1999 | Griffiths et al. | |
| 6,187,306 B1 | 2/2001 | Pardoll et al. | |
| 6,280,962 B1 | 8/2001 | Cohen | |
| 6,322,989 B1 | 11/2001 | Cohen | |
| 6,387,639 B1 | 5/2002 | Posner et al. | |
| 6,475,804 B1 | 11/2002 | Lohse | |
| 6,645,465 B2 | 11/2003 | Hanash et al. | |
| 6,667,160 B2 | 12/2003 | Fine | |
| 7,205,117 B1 | 4/2007 | Robertson et al. | |
| 7,282,345 B1 | 10/2007 | Hancock et al. | |
| 7,402,403 B1 | 7/2008 | Robertson et al. | |
| 8,114,604 B2 | 2/2012 | Robertson et al. | |
| 8,574,848 B2 | 11/2013 | Robertson et al. | |
| 8,592,169 B2 | 11/2013 | Robertson et al. | |
| 8,722,339 B2 | 5/2014 | Robertson et al. | |
| 2002/0168696 A1 | 11/2002 | Hanash | |
| 2003/0008332 A1 | 1/2003 | Ryan et al. | |
| 2003/0049651 A1 | 3/2003 | Luo et al. | |
| 2003/0049692 A1 | 3/2003 | Latov et al. | |
| 2003/0099639 A1 | 5/2003 | Rikihisa et al. | |
| 2003/0138860 A1 | 7/2003 | Robertson et al. | |
| 2003/0232399 A1 | 12/2003 | Robertson et al. | |
| 2005/0084904 A1 | 4/2005 | Laal et al. | |
| 2005/0276485 A1 | 12/2005 | Mori | |
| 2006/0141547 A1 | 6/2006 | Das et al. | |
| 2007/0172487 A1 | 7/2007 | Shih et al. | |
| 2007/0224174 A1 | 9/2007 | Kang et al. | |
| 2008/0108084 A1 | 5/2008 | Robertson et al. | |
| 2008/0153113 A1 | 6/2008 | Robertson et al. | |
| 2008/0213921 A1 | 9/2008 | Robertson et al. | |
| 2008/0305476 A1 | 12/2008 | Robertson et al. | |
| 2009/0176319 A1 | 7/2009 | Robertson et al. | |
| 2011/0086061 A1 | 4/2011 | Robertson et al. | |
| 2012/0115749 A1 | 5/2012 | Robertson et al. | |
| 2013/0090251 A1 | 4/2013 | Robertson et al. | |
| 2014/0080736 A1 | 3/2014 | Robertson et al. | |

FOREIGN PATENT DOCUMENTS

| | | |
|---|---|---|
| EP | 0236606 | 6/1992 |
| EP | 0684477 | 11/1995 |
| EP | 1200832 | 5/2006 |
| GB | 2395270 | 5/2004 |

(Continued)

OTHER PUBLICATIONS

Definition of "monocyte" in On-line Medical Dictionary downloaded on Feb. 5, 2005 from url. www.cancerweb.ncl.ac.uk.

"Cell and Molecular Biology of Vertebrate Hard Tissues", Ciba Foundation Symposium 136, 2000.

GB0725239.8 Search Report dated Apr. 24, 2008.

(Continued)

*Primary Examiner* — Jacob Cheu

(74) *Attorney, Agent, or Firm* — Finnegan, Henderson, Farabow, Garrett & Dunner LLP.

(57) ABSTRACT

The application generally relates to the field of diagnostic or prognostic assays and in particular relates to assays for the detection of antibodies in a sample comprising patient bodily fluid, wherein such antibodies are used as biological markers of a disease state or disease susceptibility. The assay is based on cross-titration of both the patient bodily fluid to be tested for the antibody and an antigen used to detect the antibody by specific binding.

5 Claims, 12 Drawing Sheets

(56) References Cited

FOREIGN PATENT DOCUMENTS

| GB | 2426581 | 11/2006 |
|---|---|---|
| GB | 2007003486 | 9/2007 |
| JP | 7294530 | 11/1995 |
| JP | 9189702 | 7/1997 |
| JP | 11-230966 | 8/1999 |
| WO | 8901153 | 2/1989 |
| WO | 9213065 | 8/1992 |
| WO | 9311236 | 6/1993 |
| WO | 9321529 | 10/1993 |
| WO | 9423728 | 10/1994 |
| WO | 9600084 | 1/1996 |
| WO | 9603502 | 2/1996 |
| WO | 9711715 | 4/1997 |
| WO | 9714794 | 4/1997 |
| WO | 9855872 | 6/1998 |
| WO | 9958978 | 11/1999 |
| WO | 9958979 | 11/1999 |
| WO | 0026668 | 5/2000 |
| WO | 0034787 | 6/2000 |
| WO | 0111372 | 2/2001 |
| WO | 02059617 | 8/2002 |
| WO | 2004044590 | 5/2004 |
| WO | 2006126008 | 11/2006 |
| WO | 2008032084 | 3/2008 |

OTHER PUBLICATIONS

"National Library of Medicine Gateway MeSH term definition downloaded from the Web", Apr. 23, 2009.
"PCT/GB2007/003486 International Search Report and Written Opinion, mailed Dec. 19, 2007".
"PCT/GB2008/004260 International Search Report and Written Opinion, mailed Feb. 27, 2009".
U.S. Appl. No. 10/534,773 , Notice of Allowance dated Jul. 9, 2013, 10 pages.
U.S. Appl. No. 10/534,773 , Office Action dated Feb. 22, 2013, 11 pages.
U.S. Appl. No. 10/534,773 , Office Action dated Sep. 8, 2011, 12 pages.
U.S. Appl. No. 10/534,773 , Office Action dated Jun. 12, 2012, 15 pages.
U.S. Appl. No. 10/534,773 , Office Action dated May 28, 2010, 18 pages.
U.S. Appl. No. 10/534,773 , Office Action dated Jan. 3, 2011, 19 pages.
U.S. Appl. No. 10/534,773 , Office Action dated Dec. 8, 2009, 26 pages.
U.S. Appl. No. 11/681,830 , Final Office Action dated Jul. 3, 2013, 18 Pages.
U.S. Appl. No. 11/681,830 , Office Action dated Oct. 26, 2010, 10 pages.
U.S. Appl. No. 11/681,830 , Office Action dated Apr. 27, 2011, 10 pages.
U.S. Appl. No. 11/681,830 , Office Action dated Dec. 5, 2012, 19 pages.
U.S. Appl. No. 11/814,516 , Non-Final Office Action dated May 23, 2013, 9 pages.
U.S. Appl. No. 11/854,050 , Notice of Allowance dated May 30, 2013, 6 pages.
U.S. Appl. No. 11/854,050 , Office Action dated Dec. 17, 2009, 10 pages.
U.S. Appl. No. 11/854,050 , Office Action dated Feb. 1, 2011, 10 pages.
U.S. Appl. No. 11/854,050 , Office Action dated Jul. 13, 2010, 5 pages.
U.S. Appl. No. 12/343,047 , Final Office Action dated Jun. 5, 2013, 24 pages.
U.S. Appl. No. 12/343,047 , Office Action dated Apr. 5, 2012, 18 pages.
U.S. Appl. No. 12/343,047 , Office Action dated Nov. 26, 2012, 19 pages.
U.S. Appl. No. 12/343,047 , Office Action dated Sep. 12, 2011, 42 pages.
U.S. Appl. No. 12/967,719 , Office Action dated Jun. 1, 2012, 12 pages.
U.S. Appl. No. 12/967,719 , Office Action dated Oct. 27, 2011, 30 pages.
U.S. Appl. No. 13/438,344 , Non-Final Office Action dated Mar. 20, 2013, 7 pages.
Aaronson et al., "Characterization of Murine Sarcoma Virus (KIRSTEN) Transformation of Mouse and Human Cells", J. Gen. Virol., 1971, 13: 245-252; ATCC accession No. CRL 1569, 245-252.
Agrawal et al., "Cancer-associated MUC1 mucin inhibits human T-cell proliferation, which is reversible by IL-2", Nature Medine, Jan. 1998, 4(1):43-49.
Ambrosini et al., "A novel anti-apoptois gene lymphoma, survivin, expressed in cancer and lymphone", Nature Med, 1997, 3(8), 917-21.
Angelopoulou et al., "Detection of the TP53 Tumour Suppressor Gene Product and p53 Auto-antibodies in the Ascites of Women with Ovarian Cancer", European Journal of Cancer, vol. 33, No. 1, Jan. 1997, pp. 115-121.
Anker et al., "K-ras mutations are found in DNA extracted from the plasma of patients with colorectal cancer", Gastroenterology, Apr. 1997, vol. 112, No. 4, 1114-1119.
Aparecida et al., "Value of CEA Level Determination in Gallbladder Bile in the Diagnosis of Liver Metastases Secondary to Colorectal Adenocarcinoma", Sao Paulo Medical Journal, vol. 119, No. 3, May 2001, pp. 110-113.
Apostolopoulos et al., "MUC1 Cross-reactive Gala(1,3)GAL antibodies in humans switch immune responses from cellular to humoral", Nature Medicine, 1998, vol. 4, 315-320.
Asano et al., "Presence of anti-AFT-antibody producing B cells in peripheral blood lymphocyte of hepatocellular carcinoma patient", Nippon Shokakibyo Gakkai Zasshi, Feb. 1984, 81(2):278.
Ayala et al., "Human Chorionic Gonadotropin Immunoreactivity in Serum of Patients With Malignant Neoplasms", Am J Reprod Immuno., Apr.-May 1983, 3(3), 149-51.
Baechstrom et al., "Purification and characterization of sialyl-Le(a)-carrying mucins of human bile; evidence for the presence of MUC1 and MUC3 apoproteins." J Biol Chem. May 20, 1994;269(20):14430-7., 14430-7.
Barak et al., "Clinical utility of cytokeratins as tumor markers", Clin Biochem, Jul. 2004, 37(7), 529-40.
Barrette et al., "Quantifying Specific Antibody Concentrations by Enzyme-Linked Immunosorbent Assay Using Slope Correction", Clinical and Vaccine Immunology, Jul. 2006, vol. 13, No. 7, 802-805.
Baselga et al., "Phase II Study of Weekly Intravenous Recombinant Humanized Anti-p185 HER2 Monoclonal Antibody in Patients with HER2/neu-Overexpressing Metastatic Breast Cancer", J. Clin Oncol., 1996, 14(3), 737-744.
Batra et al., "Expression of the Human MUC1 Mucin cDNA in a Hamster Pancreatic Tumor Cell Line HP-1", Int. J. Pancreatology, 1992, 12:271-283.
Beatty et al., "Biochemical Characterization of the Soluble Form of Tumor Antigen MUC1 Isolated from Sera and Ascites Fluid of Breast and Pancreatic Cancer Patients", Clinical Cancer Research, 2001, vol. 7, 781-787.
Beatty et al., "Measurement of monoclonal antibody affinity by non-competitive enzyme immunoassay", J Immunol Methods. Jun. 26, 1987;100(1-2):173-9., 173-9.
Bellone et al., "Cancer immunotherapy: synthetic and natural peptides in the balance", Immunology Today, 1999, 20, pp. 457-462.
Ben-Efraim , "One Hundred Years of Cancer Immunotherapy: A Critical Appraisal", Tumor Biology, 1999, vol. 20(1), pp. 1-24.
Ben-Mahrez et al., "Detection of circulating antibodies against of c-myc protein in cancer patient sera", British Journal of Cancer, vol. 57, Issue 6, Jun. 1988, pp. 529-534.
Bhatti et al., "Circulating Immunobiologic Markers in Prostatic Cancer and their Modulation by Surgical/Hormonal Therapy", Journal of Tumor Marker Oncology, vol. 9, Issue 2, Summer 1994, pp. 125-131.

(56) References Cited

OTHER PUBLICATIONS

Blackwood et al., "Functional Analysis of the AUG- and CUG-Initiated Forms of the c-Myc Protein", Molecular Biology of the Cell, 1994, 5: 597-609, 597-609.
Block et al., "Use of targeted glycoproteomics to identify serum glycoproteins that correlate with liver cancer in woodchucks and humans", Proc Natl Acad Sci USA, Jan. 18, 2005, 102(3), 779-84.
Booyse et al., "Isolation and characterization of a urokinase-type plasminogen activator (MR=54,000) from cultured human epithelial cells indistringuishable from urinary urokinase", J Biol Chem, 1984, 259(11), 7198-205.
Braun et al., "Cytokeratin-Positive Cells in the Bone Marrow and Survival of Patients with Stage I, II, or III Breast Cancer", N Engl J. Med, 2000, 342:8, 525-533.
Brichory et al., "An Immune Response Manifested by the Common Occurrence of Annexins I and II Autoantibodies and High Circulating Levels of IL-6 in Lung Cancer", PNAS, 2001, 98(17):9824-9829.
Butler et al., "Osteopontin—Structure and biological activity", CBA Foundation Symposia, 1988, 136, 203-206.
Byers, "What can randomized controlled trials tell us about nutrition and cancer prevention?", CA Cancer Journal, vol. 49, No. 6, Nov./Dec. 1999, pp. 353-361.
Callans et al., "Raf-1 Protein Expression in Human Breast Cancer Cells", Ann Surg Oncol, Jan. 1995, 2(1):38-42.
Canevari et al., "1975-1995 Revised anti-cancer serological response: Biological significance and clinical implications", Annals of Oncology, 1996, vol. 7, pp. 227-232.
Capella et al., "Frequency and Spectrum of Mutations at Codons 12 and 13 of the C-K-ras Gene in Human Tumors", Environ Health Perspectives, 1991, 93: 125-131.
Carlsson et al., "Titration of antibodies to *Salmonella* O Antigens by Enzyme-Linked Immunosorbent Assay", Infection and Immunity, vol. 6, No. 5, Nov. 1972, 6 Pages.
Casiano et al., "Tumor-associated Antigen Arrays for the Serological Diagnosis of Cancer", Molecular & Cellular Proteomics, 2006, 1745-1759.
Cervello et al., "Cyclooxygenases in hepatocellular carcinoma", World J. Gastroenterol, Aug. 28, 2006, 12(28), 5113-5121.
Chapman et al., "Autoantibodies in breast cancer: their use as an aid to early diagnosis", Annals of Oncology, Mar. 7, 2007, vol. 18, 868-873.
Chapman et al., "Autoantibodies in lung cancer: posibilities for early detection and subsequent cure", Thorax, Sep. 26, 2007, 0:1-6. doi:10.1136/thx.2007.083592.
Chari et al., "Partial-Purification of Inhibin from Human Testicular Extracts", ACTA Endocrinologia, 1977, 85 Suppl 212, 215-219.
Chen, "A testicular antigen aberrantly expressed in human cancers detected by autologous antibody screening", Proc. Nat. Acad. Sci, 1997, 94, 1914-1918.
Chinni et al., "Humoral Immune Responses to Cathepsin D and Glucose-regulated Protein 78 in Ovarian Cancer Patients", Clinical Cancer Research, Sep. 1997, 3, 1557-1564.
Clemmensen et al., "Purification and characterization of a novel, oligomeric, plasminogen kringle 4 binding-protein from human plasma -tetranectin", Eur J. Biochem, 1986, 156(2), 237-333.
Coomber et al., "Characterisation and clinicopathological correlates of serum anti-p53 antibodies in breast and colon cancer", J Cancer Res Clin Oncol, 1996, 122(12):757-62.
Coussens et al., "Tyrosine kinase receptor with extensive homology to EGF receptor shares chromosomal location with neu oncogene", Science, vol. 230, Sep. 20, 1985, 8 Pages.
Croce et al., "Expression of monoclonal-antibody-defined antigens in fractions isolated from human breast carcinomas and patient's serum", Cancer. Immunol. Immunother., 1995, vol. 40, 132-137.
Dahlberg, "Enzyme-Linked Immunosorbent Assay for Titration of Haemophilus influenzae Capsular and O Antigen Antibodies", Journal of Clinical Microbiology, Aug. 1980, vol. 12, No. 2, 185-192.
Deguchi et al., "Autoantibody to Human c-myc Oncogene Product in Autoimmune Patient's Sera", Int. Arch. Allergy Appl. Immunol., 1988, vol. 87, 313-316.
Denton et al., "Induction of antibody responses to breast carcinoma associated mucins using synthetic peptide constructs as immunogens", Cancer Letters, 1993, vol. 70, 143-150.
Devine et al., "Circulating Mucins as Tumor Markers in Ovarian Cancer", Anticancer Res. 12(3), May 1992, 709-17.
Diamandis et al., "Immunoassay", Academic Press, San Diego, CA, 1996.
Diamandis, "Human tissue kallikrein gene family: applications in cancer", Cancer Lett, Jun. 2005, 224(1), 1-22.
Diamandis et al., "Human Tissue Kallikreins: A Family of New Cancer Biomarkers", Clin. Chem, Aug. 2002, 48(8), 1198-1205.
Diamandis et al., "The new human kallikrein gene family: implications in carcinogenesis", Trends Endocrinol Metab, Mar. 2000, 11(2), 54-60.
Disis et al., "High-Titer HER-2/neu Protein-Specific Antibody Can Be Detected in Patients With Early-Stage Breast Cancer", Journal of Clinical Oncology, 1997, vol. 15, 3363-3367.
Downward et al., "Close similarity of epidermal growth factor receptor and v-erb-B oncogene protein sequences", Nature, 1984, 307, 521-527.
Dsouza et al., "Collagen-induced morphogenesis and expression of the a2-integrin subunit is inhibited in c-erbB2-transfected human mammary epithelial cells", Oncogene, 1993, 8, 1797/1806.
D'Souza et al., "Collagen-induced morphogenesis and expression of the alpha 2-integrin subunit is inhibited in c-erbB2-transfected human mammary epithelial cells", Oncogene 8(7), 1993, 1797-q806.
Duffy, "Carcinoembryonic antigen", Clin. Chem, Apr. 2001, 47(4), 624-30.
Ellis et al., "A monoclonal antibody, NCRC-11, raised to human breast carcinoma. 1. Production and immunohistological characterization", Histopathology, 1984, 8: 501-516.
Fateh-Moghadam et al., "Sensible use of tumour markers", Verlag GMBH, 1993.
Fernandez-Madrid et al., "Autoantibodies to Annexin XI-A and Other Autoantigens in the Diagnosis of Breast Cancer", Cancer Research, vol. 64, issue 15, Aug. 1, 2004, pp. 5089-5096.
Fishman et al., "Application of autoantibodies to cancer therapy: A new concept", The 9th International Congress of Immunology, 1995, 664.
Fossa et al., "Identification of a nucleolar protein No55 as a tumour-associated auto-antigen in patients with prostate cancer", Br J Cancer 83(6), 2000, 743-9.
Frazer, "Is vaccine therapy the future in cancer prevention?", Expert Opinion on Pharmacotherapy, 2004, 5(12), pp. 2427-2434.
Gasperi-Campani et al., "Chromosomal alterations, biological features and in vitro chemosensitivity of SCLC-R1, a new cell line from human metastatic small cell lung carcinoma", European Journal of Cancer, Apr. 1998, vol. 34, No. 5, 724-730.
Gerke, "Annexins: From Structure to Function", Physiological Reviews, vol. 82, 2002, 331-371.
Giardina, "Effect of antigen coating . . . ", Clin. Diagnostic Lab. Immunol., 2003, vol. 10, 1136-1140.
Gnudi et al., "Adenovirus-Mediated Gene Transfer of Dominant Negative Rasasn17 in 3T3L 1 Adipocytes Does Not Alter Insulin-Stimulated PI3-Kinase Activity of Glucose Transport", Mol. Endocrinol., 1997, 11, 67-76.
Gourevitch et al., "Polymorphic epithelial mucin (MUC-1)-containing circulating immune complexes in carcinoma patients", British Journal of Cancer, Oct. 1995, 72, 934-938.
Goydos et al., "A Phase I Trial of a Synthetic Mucin Peptide Vaccine", J. Surgical Res., 1996, 63: 298-304.
Graham et al., "The polymorphic epithelial mucin: potential as an immunogen for a cancer vaccine", Cancer Immunol. Immunother, 1996, 42:71-80.
Granziero et al., "Adoptive immunotherapy prevents prostate cancer in a transgenic animal model", Eur J Immunol., Apr. 1999, vol. 29(4), pp. 1127-1138.
Graves et al., "Malignancy-induced autoimmunity to MUC1: initial antibody characterization", J. Peptide Res., 2005, 66: 357-363.
Green et al., "Serum p53 Auto-antibodies: Incidence in Familial Breast Cancer", European Journal of Cancer, 1994, vol. 30A, 580-584.

(56) References Cited

OTHER PUBLICATIONS

Gregory, JR et al., "alpha-Fetoprotein and beta-Human Chorionic Gonadotropin Their Clinical Significance as Tumour Markers", Drugs, vol. 57, No. 4, Apr. 1999, 5 Pages.

Griffiths et al., "Assignment of the polymorphic intestinal mucin gene MUC2 to chromosome-11p15", Ann Hum Genet, 1990, 54:277-85.

Gure, "Human Lung Cancer Antigens Recognized by Autologous Antibodies: Definition of a Novel cDNA Derived from the Tumor Suppressor Gene Locus on Chromosome 3p21.3", Ludwig Institute for Cancer Research, 1998, 1034-1040.

Haga et al., "Partial Purification and Characterization of CA19-9 Antigen from the Ascitic Fluid of a Patient with Pancreatic Cancer", Clin Biochem, Oct. 22, 1989, (5)363-8.

Harlow et al., "Antibodies A Laboratory Manual", Cold Spring Harbor Press, 1989, 141-241.

Harlow et al., "Antibodies: A Laboratory Manual", Cold Spring Harbor Laboratory, 1988, 562-563.

Hayes, "Serum tumor markers for breast cancer", Anticancer Drugs, 1995, vol. 6, suppl. 2, 26-27 (Abstract).

He et al., "Proteomics-based identification of alpha-enolase as a tumor antigen in non-small lung cancer", Cancer Sci, Aug. 2007, 98(8), 1234-1240.

Hehir et al., "C-myc Oncogene Expression: A Marker for Females at Risk of Breast Carcinoma", Journal of Surgical Oncology, 1993, vol. 54, 207-210.

Hill et al., "Nature of Carcinoembryonic Antigen Purified from Malignant Ascitic Fluid of Serous Cystadenocarcinoma of the Ovary", Molecular Immunology, 1981, vol. 18, No. 7, 647-653.

Hinoda et al., "Detection of a Circulating Antibody Against a Peptide Epitope on a Mucin Core Protein, MUC1, in Ulcerative Colitis", Dept. of Internal Medicine (Section 1), Sapporo Medical College S-1, W-16, Sapporo, Japan, 1991, 163-168.

Hirasawa et al., "Natural Autoantibody to MUC1 Is a Prognostic Indicator for Non-Small Cell Lung Cancer", Am J Respir Crit Care Med, 2000, 161:589-594.

Hirasawa et al., "KL-6, a human MUC1 mucin, is chemotactic for human fibroblasts.", American Journal of Respiratory Cell and Molecular Biology [1997, 17(4):501-507].

Houghton et al., "Detection of Cell Surface and Intracellular Antigens by Human Monoclonal Antibodies—Hybrid Cell Lines Derived from Lymphocytes of Patients with Malignant Melanoma", J. Exp. Med., Jul. 1983, vol. 158, 53-65.

Hsu et al., "GRP78 expression correlates with histologic differentiation and favorable prognosis in neuroblastic tumors", Int J Cancer, Mar. 1, 2005, 113, 920-7.

Hudelist et al., "Use of high-throughput protein array for profiling of differentially expressed proteins in normal and malignant breast tissue", Breast Cancer Res treat., Aug. 2004, vol. 86(3), 281-91.

Hudson et al., "Method for Testing Antiserum Titer and Avidity in Nephelometric Systems", Clinical Chemistry, 1981, vol. 27, No. 11, 1838-1844.

Huhtala et al., "Excretion of a tumor associated trypsin-inhibitor (TATI) in urine of patients with Gynecological Malignancy", Int J Cancer, 1983, vol. 31(6), 711-714.

Ibrahim et al., "Expression of biomarkers (p53, transforming growth factor alpha, epidermal growth factor receptor, c-erbB-2/neu and the proliferative cell nuclear antigen) in oropharyngeal squamous cell carcinomas", Oral Oncology, Elsevier Science, Oxford, GB, May 1999, 35(3):302-313.

Israeli, "Molecular Cloning of a Complementary DNA Encoding a Prostate-specific Membrane Antigen", Cancer Res., 1993, 53:227-30.

Jager, "Cancer-Testis Antigens and INGI Tumor Suppressor Gene Product Are Breast Cancer Antigens: Characterization of Tissue-specific INGI Transcripts and a Homologue Gene", Cancer Res, Dec. 15, 1999, vol. 59(24), 6197-6204.

Jager et al., "Identification of a tissue-specific putative transcription factor in breast tissue by serological screening of a breast cancer library", Cancer Res, 2001, vol. 61(5), 2055-61.

Jais et al., "Association of Serum Antibodies against p53 protein with poor survival in patients with Zollinger-Ellison syndrome", Gastroenterology, Elsevier, Philadelphia, PA, Jan. 1998, vol. 114, No. 1, 37-43.

Jalanko et al., "Immunochemical properties of alpha-fetoprotein (AFP) and antibodies to autologous AFT", Immunol. Commun, 1978, vol. 7, No. 2, 209-222.

Janeway et al., Immunobiology, 5th ed., 2001.

Janeway et al., "Competitive Inhibition Assay for Antigen in Unknown Samples", Immunobiology downloaded from url www.ncbi.nlm.nih.gov/books/bv.fcgi?rid=imm.figgrp.2410, 2001, 106-108 & 260-263.

Jerome et al., "A Survivor of Breast Cancer with Immunity to MUC-1 Mucin, and Lactational Mastitis", Cancer Immunology and Immunotherapy, Jan. 1997, Berlin, DE, vol. 43, No. 6, 355-360.

Karanikas et al., "Antibody and T Cell Responses of Patients with Adenocarcinoma Immunized with Mannan-MUC1 Fusion Protein", J. Clin Invest. vol. 100, No. 11, 1997, 2783-92.

Karlan et al., "Peritoneal Serous Papillary Carcinoma, A Phenotypic Variant of Familial Ovarian Cancer: Implications for Ovarian Cancer Screening", American Journal of Obstetrics & Gynecology, Apr. 1999, Mosby, St. Louis, MO, vol. 180, No. 4, 917-928.

Kasof et al., "Livin, a novel inhibitor of apoptosis protein family", J Biol Chem, 2000, vol. 276(5), 3238-46.

Kawahara, "Use of Four Monoclonal Antibodies to Detect Tumor Markers", Cancer, 1986, vol. 58, 2008-2012.

Kiefer et al., "The CDNA and derived amino-acid sequence for human Osteopontin", Nucleic Acids Res, 1989, 17(8), 3306.

Kim et al., "Human kallikrein gene 5 (KLK5) expression is an indicator of poor prognosis in ovarian cancer", Br. J. Cancer, 2001, vol. 84(5), 643-650.

Kim et al., "Clinicopathologic significance of the basal-like subtype of breast cancer: a comparison with hormone receptor and Her2/neu-overexpressing phenotypes", Hum Pathol.—Rpub Jul. 18, 2006, Sep. 2006, 37(9), 1217-26.

Kirchoff, "A major human epididymis-specific cDNA encodes a protein with sequence homology to extracellular proteinase-inhibitors", Biology of Reproduction, 1991, 45(2), 350-357.

Kohno et al., "Detection of Soluble Tumor-associated Antigens in Sera and Effusions Using Novel Monoclonal Antibodies, KL-3 and KL-6, against Lung Adenocarcinoma", Jpn. J. Clin. Oncol. 18: 203-216, 1988.

Kotera et al., "Humoral Immunity against a Tandem Repeat Epitope of Human Mucin MUC-1 in Sera from Breast, Pancreatic, and Colon Cancer Patients", Cancer Research, 1994, vol. 54, 2856-2860.

Krause et al., "SeroGRID: an improved method for the rapid selection of antigens with disease related immunogenicity", J Immunol Methods, Dec. 2003, vol. 283, 261-7.

Kumar et al., "Standardisation and comparison of serial dilutions and single dilution enzyme linked immunosorbent assay (ELISA) using different antigenic preparations of the Babesia (Theileria) equi parasite", Veterinary Research, vol. 34, No. 1, 2003, 71-83.

Kuralay et al., "Diagnostic Usefulness of Tumour Marker Levels in Pleural Effusions of Malignant and Benign Origin", Clinica Chimica Acta, 2000, vol. 300, 43-55.

Kutteh et al., "Immunologic Characterization of Tumor Markers in Human Ovarian Cancer Cell Lines", Journal of the Society for Gynecologic Investigation, 1996, vol. 3, No. 4, 216-222.

Laeng et al., "Anti-Neural Autoantibodies, types 1 and 2: Their Utility in the Study of Tumors of the Nervous System", Acta Neuropathol, 1998, 329-339.

Lafond et al., "Autoantibodies to c-myc protein: elevated levels in patients with African Burkitt's lymphoma and norman Ghanians", Autoimmunity, 1992, vol. 13, No. 3, 215-224.

Lai et al., "Presence of Serum Anti-P53 Antibodies is Associated with Pleural Effusions and Poor Prognosis in Lung Cancer Patients", Clinical Cancer Research, 1998, vol. 4, 3025-3030.

Lawniczak et al., "The Search for Tumor-Associated Proteins in Pleural Effusions by Means of Moniclonal Antibodies and a Dot Blot Assay", Lung, 1992, vol. 170, 65-74.

(56) References Cited

OTHER PUBLICATIONS

Lederman et al., "A Single Amino Acid Substitution in a Common African Allele of the CD4 Molecule Ablates Binding of the Monoclonal Antibody, OKT4", Molecular Immunology, 1991, vol. 28, No. 11, 1171-1181.

Li et al., "B-Endorphin omission analogs: Dissociation of immunoreactivity from other biological activities", Proc. Natl. Acad. Sci., Jun. 1980, vol. 77, No. 6, 3211-3214.

Lindner et al., "Specific Detection of His-Tagged Proteins with Recombinant Anti-His Tag scFv-Phosphatase or scFv-Phage Fusions", Bio Techniques, 1997, 22 (1), 140-149.

Lloyd et al., "Isolation and Characterization of Ovarian Cancer Antigen CA 125 Using a New Monoclonal Antibody (VK-8) Identification As a Mucin-Type Molecule", Int. J. Cancer, 1997, 71: 842-850.

Lubin et al., "Analysis of p53 Antibodies in Patients with Various Cancers Define B-Cell Epitopes of Human p53: Distribution on Primary Structure and Exposure on Protein Surface", Cancer Research, 1993, vol. 53, pp. 5872-5876.

Luo et al., "Identification of Heat Shock Protein 90 and Other Proteins as Tumour Antigens by Serological Screening of an Ovarian Carcinoma Expression Library", British Journal of Cancer, 2002, 339-343.

Maeda et al., "Aberrant Expression of Photoreceptor-specific Calcium-binding Protein (Recoverin) in Cancer Cell Lines", Cancer Res. 2000, Apr. 1, 2000, 60(7):1914-20.

Mashino et al., "Expression of multiple cancer-testis antigen genes in gastrointestinal and breast carcinomas", Br. J. Cancer, 2001, 85(5):713-720.

Matlashewski et al., "Isolation and characterization of a human p53 cDNA clone: expression of the human p53 gene.", EMBO J., 1984, 3:3257-3262.

McIntyre et al., "Oral contraceptive usage and the expression of CA 15-3 and C-erB-2 in the saliva of healthy women", Oral Radiology and Endodontics, Dec. 1999, vol. 88, No. 6, 687-690.

Meichenin et al., "Tk, a new colon tumor-associated antigen resulting from altered O-glycosylation", Cancer Res, Oct. 1, 2000, 60 (19), 5499-507.

Mercer, "Use of Multiple Markers to Enhance Clinical Utility", Immunology Series, 1990, vol. 53, 39-54.

Microbix Biosystems Inc., "Antigen titration using the Microbix IgG ELISA", Product Technical Bulletin, URL://http://web.archive.org/web/2005 0526 2316 23/http://www.microbix.com/products/PDFs/Tb-93-1AntigenTitraionousingtheMicrobixlgG+ELISA.pdf, 2005.

Mineva et al., "Differential expression of alphaB-crystallin and Hsp27-1 in anaplastic thyroid carcinomas because of tumor-specific alphaB-crystallin gene (CRYAB) silencing", Cell Stress & Chaperones, Autumn 2005, 10(3):171-84.

Moingeon, "Strategies for designing vaccines eliciting Th1 responses in humans", Journal of Biotechnology, 2002, vol. 98, pp. 189-198.

Molina et al., "Use of serial carcinoembryonic antigen and CA 15.3 assays in detecting relapses in breast cancer patients", Breast Cancer Res Treat, 1995, 36:41-48.

Moll et al., "The Catalog of Human Cytokeratins: Patterns of Expression in Normal Epithelia, Tumors and Cultured Cells", Cell, Nov. 31, 1982, 31(1), 11-24.

Montenarh et al., "P53 Autoantibodies in the Sera, Cyst and Ascitic Fluids of Patients with Ovarian Cancer", International Journal of Oncology, 1998, vol. 13, 605-610.

Mudenda et al., "The relationship between serum p53 autoantibodies and characteristics of human breast cancer", CR J Cancer, 1994, 69:4445-4449.

Munemitsu et al., "Regulation of intracellular B-catenin levels by the adenomatous polyposis coli (APC) tumor-suppressor protein", PNAS, 1995, 92: 3046-50.

Munoz et al., "New experimental criteria for optimization of solid-phase antigen concentration and stability in ELISA", J. Immunol. Methods, 1986, 20:137-44.

Muraki et al., "Assessment of serum CYFRA 21-1 in lung cancer", Cancer, Apr. 1996, 77(7), 1274-7.

Muraki et al., "Serum CYFRA 21-1 in Lung Cancer", Fourth Dept. of Internal Medicine, 1996, 1274-1277.

Narod, "Genetic epidemiology of prostate cancer", BBA-Reviews on Cancer, Jan. 1999, vol. 1423, No. 2, F1-F13.

Nery, "Isolation and Partial Characterization of Macromolecular Urinary Aggregates Containing Carcinoembryonic Antigen-Like Activity", Br. J. Cancer, 1974, vol. 29, No. 413.

Norum et al., "Elevated CA 125 in Breast Cancer—A Sign of Advanced Disease", Tumour Biol., Jul.-Aug. 2001, 22(4), 223-8.

Nouwen et al., "Occurrence of the mucinous differentiation antigen CA125 in genital tract and conductive airway epithelia of diverse mammalian species (rabbit, dog, monkey)", Differentiation, 1990, 45:192-198.

Nustad et al., "Epitopes on CA 125 from Cervical Mucus and Ascites Fluid and Characterization of Six New Antibodies", Tumor Biol., 2002, 303-314.

Obiezu et al., "Human tissue kallikrein gene family: applications in cancer", Cancer Lett., Jun. 2005, 224(1), 1-22.

O'Sullivan et al., "Polymorphic epithelial mucin from the sera of advanced breast cancer patients—isolation and partial characterisation", British Journal of Cancer, 1990, vol. 61, pp. 801-808.

Pandha et al., "Cellular and humoral responses to KRAS polynucleotide vaccines", Cancer Gene Therapy, 1997, vol. 4, No. 5, 310.

Pare et al., "An enzyme-linked immunosorbent assay (ELISA) for serological diagnosis of *Neospora* sp. infection in cattle", Journal of Veterinary Diagnostic Investigation, 1995, AAVLD, Columbia MO, vol. 7, 352-359.

Pavelic et al., "Evaluation of c-myc proto-oncogene in primary human breast carcinomas", Anticancer Research, Jul.-Aug. 1991, 11(4):1421-1428.

Pedrero et al., "Annexin A1 Down-Regulation in Head and Neck Cancer Is Associated with Epithelial Differentiation Status", American Journal of Pathology, 2004, 164(1), 73-79.

Perey, "Elevated CA125 levels in patients with metastatic breast carcinoma", Br J Cancer, Oct. 1990, 62(4), 668-670.

Petrakou et al., "Preliminary Studies on the Binding of Human Autoantibodies to the MUC1 Antigen", International Journal of Oncology, 1997, vol. 11, Suppl., 902.

Petrarca et al., "Human Antibodies Against the Polymorphic Epithelial Mucin in Ovarian Cancer Patients Recognise a Novel Sequence in the Tandem Repeat Region", European Journal of Cancer, 1996, vol. 32, No. 12, 2155-2163 (Abstract only).

Pratt et al., "Estrogen activates raf-1 kinase and induces expression of EGR-1 in MCF-7 breast cancer cells", Mol Cell Biochem, Dec. 1998, 189(1-2), 119-25.

Prezas, "Overexpression of the human tissue kallikrein genes KLK4, 5, 6, and 7 increases the malignant phenotype of ovarian cancer cells", Biol. Chem., Jun. 2006, 387(6), 807-811.

Raghava et al., "Method for determining the affinity of monoclonal antibody using non-competitive ELISA: A computer program", Journal of Immunoassay, 1994, 15(2), 115-128.

Rao et al., "Detection of Human Ovarian Tumor Associated Antigens by Autologous Antibodies Isolated from Ovarian Carcinoma Ascites Fluid", Proceedings of the American Association of Cancer Research Annual Meeting, 1987, vol. 28 #1419, 358.

Rao et al., "Detection of human ovarian tumor-associated antigens by antibodies isolated from ovarian carcinoma ascitic fluid", Am J Obstet Gynecol, Jul. 1998, vol. 159, 94-98.

Rasmussen et al., "An ELISA for the detection of anti-neutrophil cytoplasm antibodies (ANCA)", Journal of Immunological Methods, vol. 127, No. 1, Feb. 20, 1990, pp. 139-145.

Reddish et al., "Pre-immunotherapy serum CA27.29 (MUC-1) mucin level and CD69+ lymphocytes correlate with effects of Theratope siayl-Tn-KLH cancer vaccine in active specific immunotherapy", Cancer Immunol. Immunother, 1996, 42: 303-309.

Reiter et al., "Prostate stem cell antigen: A cell surface marker overexpressed in prostate cancer", Proc Nat. Acad. Sci., 1998, 95:1735-1740.

Riddle et al., "The preparation, identification and assey of prolactin—A hormone of the anterior pituitary", Am J. Physiol, 1933, 105(1), 191-216.

(56) References Cited

OTHER PUBLICATIONS

Robertson et al., "Assessment of Four Monoclonal Antibodies as Serum Markers in Breast Cancer", Eur. J. Cancer, 1990, 26: 1127-1132.

Robertson et al., "Prospective assessment of the role of five tumour markers in breast cancer", Cancer Immunol. Immunother., 1991, 33:403-410.

Robertson et al., "Radioimmunohistochemistry of Epidermal Growth Factor Receptor in Breast Cancer", Archives of Pathology and Laboratory Medicine, 2001, 126:177-81.

Rosenberg et al., "Modulation of Androgen and Progesterone Receptors by Phytochemicals in Breast Cancer Cell Lines", Biochem Biophys Res Commun., 1998, 248: 935-939.

Rughetti et al., "Human B-Cell Immune Response to the Polymorphic Epithelial Mucin1", Cancer Research, Jun. 1, 1993, 53, pp. 2457-2459.

Rusciano, "Conomitant Purification of Prostatic Carcinoma Tumor Markers from Human Seminal Fluid Under Nondenaturing Conditions", Clinical Chemistry, 1988, vol. 34, No. 12, 2528-2532.

Sahin et al., "Human neoplasms elicit multiple specific immune responses in the autologous host", PNAS, 1995, vol. 92, 11810-11813.

Sakurai et al., "Differential expression of the glycosylated forms of MUC1 during lung development", European Journal of Histochemistry 2007, vol. 51 issue 2 (Apr.-Jun.); 95-102.

Sandrin, "Natural human anti-Gala(1,3)Gal antibodies react with human mucin peptides", Glycoconjugate Journal, 1997, 14:97-105.

Scanlan et al., "Characterization of Human Colon Cancer Antigens Recognized by Autologous Antibodies", International Journal of Cancer vol. 76, 1998, 652-658.

Schjetlein et al., "Choice of Standard Plasma for Diagnosis and Quantitation of Lupus Anticoagulants", Thrombosis Research, 1993, 72:287-294.

Schneider, "P53 protein, EGF Receptor, and Anti-P53 Antibodies in Serum from Patients with Occupationally Derived Lung Cancer", British Journal of Cancer, 1999, vol. 80, No. 12, 1987-1994.

Scully et al., "BRCA1 is a component of the RNA polymerase II holoenzyme", PNAS, 1997, 94: 5605-10.

Seabury et al., "Evaluation of a new serum testing method for detection of prostate cancer", J Urol, Jul. 2002, 168(1):93-9.

Seitz et al., "Genetic Background of Different Cancer Cell Lines Influences the Gene Set Involved in Chromosome 8 Mediated Breast Tumor Suppression", Genes Chromosomes Cancer, Jun. 2006, 45(6), 612-27.

Sharan et al., "Embryonic lethality and radiation hypersensitivity mediated by Rad51 in mice lacking Brca2", Nature, 1997, 386: 804-810.

Shibata et al., "Purification and Characterization of Prostate Specific Antigen from Human Urine", Biochimica et Biophysica Acta, 1997, vol. 1336, 425-433.

Sokoloff et al., "A dual-Monoclonal Sandwich Assay for Prostate-Specific Membrane Antigen: Levels in Tissues, Seminal Fluid and Urine", The Prostate, 2000, vol. 43, 150-157.

Soussi, "The humoral response to the tumor-suppressor gene-product p53 in human cancer: implications for diagnosis and therapy", Immunology Today, vol. 17, No. 8, Aug. 1996, 3 Pages.

Standker et al., "Isolation and characterization of the circulating form of human endostatin", FEBS Letters, 1997, vol. 420, 129-133.

Stearns et al., "Circulating tumor markers in breast cancer: Accepted utilities and novel prospects", Breast Cancer Research and Treatment vol. 52, Feb. 8, 1998, 239-59.

Stedman, "Stedman's Medical Dictionary 27th Edition Definition of Fluid", http://www.thomsonhc.com/pdrel/librarian, 2004, Definitions of several words 1-3 accessed Dec. 17, 2007.

Stieber et al., "A new marker in lung cancer", Cancer, Aug. 1993, 72(3), 707-13.

Stiller et al., "Immunohistochemical demonstration of alpha-fetoprotein in testicular germ cell tumors", Acta Histochem Suppl., 1986, Supp—Band 33:225-31.

Stockert et al., "A Survey of the Humoral Immune Response of Cancer Patients to a Panel of Human Tumor Antigens", Journal of Experimental Medicine, 1998, 187 (8), 1349-1354.

Strnad et al., "Simple determination of polysaccharide specific antibodies by means of chemically modified ELISA plates", Journal of Immunological Methods, Jun. 14, 1996, Elsevier Science Publishers B.V., vol. 193, No. 1, 1-7.

Stubbs et al., "Faecal Carcinoembryonic Antigen (CEA) in Patients with Large Bowel Cancer", European Journal of Surgical Oncology, 1987, vol. 13, 433-436.

Su et al., "Association between Wild Type and Mutant APC Gene Products", Cancer Res., 1993, 53:2728-2731.

Szala et al., "Molecular cloning of cDNA for the carcinoma-associated antigen GA733-2", Proceedings of the National Academy of Sciences of the United States of America, vol. 87, May 1990, pp. 3542-3546.

Szekanecz et al., "Increased production of the soluable tumor-associated Antigens CA19-9, CA125, and CA15-3 in Rheumatoid Arthritis; Potential Adhesion Molecules in Synovial Inflammation?", Annals of the New York Academy of Sciences, vol. 1108, Jun. 2007, 13 pages.

Tauchi et al., "Expression of heat shock protein-70 and c-myc protein in human breast-cancer—an immunohistochemical study", Jap J Clin Oncol, 1991, 21(4), 256-63.

Taylor-Papadimitriou, "Report on the First International Workshop on Carcinoma-Associated Mucins", Int. J. Cancer, 1991, 49:1-5.

Thomas et al., "Failure of CA19-9 to detect asymptomatic colorectal carcinoma", Br. J. Cancer, 1991, 63:975-976.

Tondini et al., "Comparison of CA15-3 and Carcinoembryonic Antigen in Monitoring the Clinical Course of Patients with Metastatic Breast Cancer", Cancer Research, 1988, vol. 48, No. 14, 4107-4112.

Toth et al., "A Carcinoembryonic Antigen (CEA) Binding Protein from Ascites Influences CEA Uptake by Macrophages", Biochemical and Biophysical Research Communications, 1990, vol. 171, No. 2, 633-640.

Treon et al., "Elevated soluble MUC1 levels and decreased anti-MUC1 antibody levels in patients with multiple myeloma", Blood, 2000, (96)6, pp. 3147-3153.

Tsai et al., "Relationship of serum alpha-fetoprotein to circulating immune complexes and complements in patients with hepatitis B surface antigen-positive hepatocellular carcinoma", Gastroenterol Jpn, Jun. 1990, 25(3), 338-93.

Tsujimoto et al., "Analysis of the structure, transcripts, and protein products of Bcl-2, the gene involved in human follicular lymphoma", PNAS USA, 1986, 83(14), 5214-8.

Van Milligen et al., "Calculation of the affinity constant KASS for solid phase antigen: A model system using monoclonal antibodies against the cat allergen Fel d I", Journal of Immunological Methods, 1993, 162:165-173.

Vang et al., "Cytokeratins 7 and 20 in Primary and Secondary Mucinous Tumors of the Ovary: Analysis of Coordinate Immunohistochemical Expression Profiles and Staining Distribution in 179 Cases", Am J. Surg Pathol, Sep. 2006, 30(9):1130-1139.

Venegas et al., "Purification and Immunochemical Characterization of Ascitic Fluid Glycoproteins Containing Certain Tumor-Associated and Blood Group Antigen Markers", Glycoconjugate Journal, 1989, vol. 6, 551-524.

Voet et al., Biochemistry, 1990, 78, 1096, 1098, year 1990 vol. 78, p. 1096-98.

Volkmann et al., "Anti-p53 autoantibodies as serological marker in different tumor-entities", Clinical Chemistry, Jul. 1995, vol. 41, No. S6 part 2, S221-S222.

Von Mensdorff-Pouilly et al., "Circulating MUC1 Antibodies in Humans are Directed to More than One Region Within the MUC1 Mucin Peptide Core", Anticancer Research, Nov.-Dec. 1997, vol. 17, 4184.

Von Mensdorff-Pouilly, "Humoral Immune Response to Polymorphic Epithelial Mucin (MUC-1) inpatients with Benign and Malignant Breast Tumours", European Journal of Cancer, 1996, vol. 32A, No. 8, 1325-1331.

Warri et al., "Anti-oestrogen Stimulation of ERBB2 Ectodomain Shedding from BT-474 Human Breast Cancer Cells with ERBB2 Gene Amplification", Eur. J. Cancer, 1996, 32A: 134-140.

(56) References Cited

OTHER PUBLICATIONS

Wolf et al., "A Tumour-Associated Antigen from the Pleural Effusion of Patients with Squamous-Cell Carcinoma of Lung", Br. J. Cancer, 1978, vol. 36, 1046-1052.
Wolf et al., "In Vitro Expression of Human p53 cDNA Clones and Characterization of the Cloned Human p53 Gene", Mol. Cell. Biol., 1985, 5(8):1887-1893.
Wolfe et al., "A Tumour-Associated Antigen from the Pleural Effusion of Patients with Squamous-Cell Carcinoma of Lung", Br. J. Cancer, 1978, vol. 36, 1046-1052.
Wu et al., "The expression of BIRC7 protein and mRNA in non-Hodgkin's lymphoma", Leukemia & Lymphoma, 47(6), 2006, 1110-6.
Xing et al., "Phase I study of synthetic MUC1 peptides in breast cancer", Int. J.Oncol., 1995, 6(6): 1283-1289.
Xu et al., "Overexpression of COX-2 in human osteosarcoma cells decreases proliferation and increases apoptosis", Cancer Res. Jul. 1, 2006;66(13), 6657-64.
Yamadori et al., "A case of non-specific interstitial pneumonia associated with primary lung cancer: possible role of antibodies to lung cancer cells in the pathogenesis of non-specific interstitial pneumonia", Respiratory Medicine, 1999, 93, 754-756.
Yamamoto et al., "Detection of auto-antibodies against c-Myc in sera from lung cancer patients", Proc. Amer. Soc. Cancer Res., 1997, 564.
Yamamoto et al., "L-Myc Overexpression and Detection of Auto-Antibodies Against L-Myc in both the Serum and Pleural Effusion from a Patient with Non-Small Cell Lung Cancer", Internal Medicine, 1997, vol. 36, No. 10, 724-727.
Yamauchi et al., "Autoantibodies to C-MYC Nuclear Protein Products in Autoimmune Disease", Immunology, Jan. 1990, 69(1):117-20.
Yang et al., "Development and evaluation of indirect ELISA for the detection of antibodies against Japanese encephalistis virus in swine", Journal of Veterinary Science, Sep. 30, 2006, vol. 7, No. 3, 271-275.
Yang et al., "Characterization of Genes Associated with Different Phenotypes of Human Bladder Cancer Cells", W. Acta Biochim Biophys Sin (Shanghai), Sep. 2006, 38(9), 601-10.
Yazici et al., "Amplification in tumors and benign tissue of breast cancer patients", Cancer Letters, vol. 107, Issue 2, Oct. 22, 1996, pp. 235-239.
Yousef et al., "Expanded Human Tissue Kallikrein Family—A Novel Panel of Cancer Biomarkers", Tumor Biol, 2002, 23, 185-192.
Zehentner et al., "Mammaglobin as a Novel Breast Cancer Biomarker: Multigene Reverse Transcription-PCR Assay and Sandwich ELISA", Clin Chem, Nov. 2004, 50(11), 2069-76.
Zehentner et al., "Mammaglobin: a candidate diagnostic marker for breast cancer", Clin Biochem., Apr. 2004, 37(4), 249-57.
Zhang et al., "Enhancement of Antibody Detection in Cancer Using Panel of Recombinant Tumor-associated Antigens", Cancer Epidermiology, Biomarkers & Prevention, 2003, vol. 12(2):136-143.
Zhu et al., "Adenocarcinoma of Duodenum and Ampoulla of Vater: Clinicopathology Study and Expression of p53, c-neu, TGF-a, CEA, and EMA", Journal of Surgical Oncology, 1996, vol. 61; 100-105.
Zielen et al., "Simple determination of polysaccharide specific antibodies by means of chemically modified ELISA plates", J. Immunol. Methods, Jun. 1996, 193(1), 1-7.
Zisman et al., "Autoantibodies to Prostate Specific Antigen in Patients With Benign Prostatic Hyperplasia", Journal of Urology, 1995, vol. 154, 1052-1055.
U.S. Appl. No. 12/343,047 , "Non-Final Office Action", Feb. 27, 2014, 35 pages.
U.S. Appl. No. 12/967,719 , "Final Office Action", Jul. 3, 2014, 9 pages.
U.S. Appl. No. 13/349,348 , "Non-Final Office Action", Jun. 13, 2014, 12 pages.
U.S. Appl. No. 11/681,830 , "Non Final Office Action" dated Nov. 25, 2013, 10 pages.
U.S. Appl. No. 11/814,516 , "Notice of Allowance" dated Dec. 27, 2013, 10 pages.
U.S. Appl. No. 12/967,719 , "Non-Final Office Action" dated Oct. 18, 2013, 12 pages.
U.S. Appl. No. 13/349,348 , "Non Final Office Action" dated Sep. 19, 2013, 13 pages.
U.S. Appl. No. 13/438,344 , "Final Office Action" dated Dec. 16, 2013, 7 pages.
Lenner et al., "Serume antibodies against p53 in relation to cancer risk and prognosis in breast cancer: a population-based epidemiological study", British Journal of Cancer, Feb. 1999, vol. 79, pp. 927-932.
International Application No. PCT/GB2007/00346281 , "International Search Report" dated Dec. 19, 2007.
Regidor et al., "Detection of p53 auto-antibodies in the aera of breast cancer patients with a new recurrence using an ELISA assay. Does a correlation with the recurrence free interval exist?", European Journal of Gynaecological Oncology, 1996, vol. 17, No. 3, pp. 192-199.
Takahashi et al., "Antibody to ras proteins in patients with colon cancer", Clin Cancer Res, vol. 1, 1995, p. 1071-1077.
Vennegoor et al., "Autoantibodies to p53 in ovarian cancer patients and healthy women: a comparison between whole p53 protein and 18-mer peptides for screening purposes", Cancer Letters, 1997, vol. 116, pp. 93-101.
Winter et al., "Development of Antibodies against p53 in Lung Cancer Patients Appears to Be Dependent on the Type of p53 Mutation", Cancer Res; vol. 52, 1992, p. 4168-4174.
"Cell and Molecular Biology and Vertebrate Hard Tissues", Ciba Foundation Symposium 136, 1988.

|   | 1 | 2 | 3 | 4 | 5 | 6 | 7 | 8 | 9 | 10 | 11 | 12 |
|---|---|---|---|---|---|---|---|---|---|---|---|---|
| A |   |   |   |   |   |   | 160nm antigen |   |   |   |   |   |
| B |   |   |   |   |   |   | 50nm antigen |   |   |   |   |   |
| C |   |   |   |   |   |   | 16nm antigen |   |   |   |   |   |
| D |   |   |   |   |   |   | 5nm antigen |   |   |   |   |   |
| E |   |   |   |   |   |   | 1.6nm antigen |   |   |   |   |   |
| F |   |   |   |   |   |   | 0.5nm antigen |   |   |   |   |   |
| G |   |   |   |   |   |   | 0.16nm antigen |   |   |   |   |   |
| H |   |   |   |   |   |   | buffer |   |   |   |   |   |

A

|   | 1 | 2 | 3 | 4 | 5 | 6 | 7 | 8 | 9 | 10 | 11 | 12 |
|---|---|---|---|---|---|---|---|---|---|---|---|---|
| A |   |   |   |   |   |   |   |   |   |   |   |   |
| B |   |   |   |   |   |   |   |   |   |   |   |   |
| C |   |   |   |   |   |   |   |   |   |   |   |   |
| D | 1:1600 |   | 1:800 |   | 1:400 |   | 1:200 |   | 1:100 |   | 1:50 |   |
| E |   |   |   |   |   |   |   |   |   |   |   |   |
| F |   |   |   |   |   |   |   |   |   |   |   |   |
| G |   |   |   |   |   |   |   |   |   |   |   |   |
| H |   |   |   |   |   |   |   |   |   |   |   |   |

IMMUNOASSAY METHODS

PRIOR RELATED APPLICATIONS

This application is a divisional application of U.S. patent application Ser. No. 11/854,050 filed Sep. 12, 2007, which claims the benefit of U.S. Provisional Application No. 60/844,158 filed Sep. 13, 2006, which is incorporated herein by reference in its entirety.

FIELD OF THE INVENTION

The invention generally relates to the field of diagnostic or prognostic assays and in particular relates to assays for the detection of antibodies in a sample comprising patient bodily fluid, wherein such antibodies are used as biological markers of a disease state or disease susceptibility.

BACKGROUND TO THE INVENTION

Many diagnostic, prognostic and/or monitoring assays rely on detection of a biological marker of a particular disease state or disease susceptibility. Such biological markers are commonly proteins or polypeptides that are characteristic of a particular disease or associated with susceptibility to disease.

In recent years it has become apparent that antibodies, and in particular autoantibodies, can also serve as biological markers of disease or disease susceptibility. Autoantibodies are naturally occurring antibodies directed to an antigen which an individual's immune system recognises as foreign even though that antigen actually originated in the individual. They may be present in the circulation as circulating free autoantibodies or in the form of circulating immune complexes consisting of autoantibodies bound to their target antigen. Differences between a wild type protein expressed by "normal" cells and an altered form of the protein produced by a diseased cell or during a disease process may, in some instances, lead to the altered protein being recognised by an individual's immune system as "non-self" and thus eliciting an immune response in that individual. This may be a humoral (i.e B cell-mediated) immune response leading to the production of autoantibodies immunologically specific to the altered protein.

WO 99/58978 describes methods for use in the detection/diagnosis of cancer which are based on evaluating the immune response of an individual to two or more distinct tumour markers. These methods generally involve contacting a sample of bodily fluid taken from the individual with a panel of two or more distinct tumour marker antigens, each derived from a separate tumour marker protein, and detecting the formation of complexes of the tumour marker antigens bound to circulating autoantibodies immunologically specific for the tumour marker proteins. The presence of such circulating autoantibodies is taken as an indication of the presence of cancer.

Assays which measure the immune response of the individual to the presence of tumour marker protein in terms of autoantibody production provide an alternative to the direct measurement or detection of tumour marker protein in bodily fluids. Such assays essentially constitute indirect detection of the presence of tumour marker protein. Because of the nature of the immune response, it is likely that autoantibodies can be elicited by a very small amount of circulating tumour marker protein and indirect methods which rely on detecting the immune response to tumour markers will consequently be more sensitive than methods for the direct measurement of tumour markers in bodily fluids. Assay methods based on the detection of autoantibodies may therefore be of particular value early in the disease process and possibly also in relation to screening of asymptomatic patients, for example in screening to identify individuals "at risk" of developing disease amongst a population of asymptomatic individuals, or to identify individuals who have developed a disease amongst a population of asymptomatic individuals. In addition, assay methods based on the detection of autoantibodies may be of particular value early in the disease process and possibly also may be used to identify individuals who have developed a disease amongst a population of symptomatic individuals. Furthermore, they may be useful for earlier detection of recurrent disease. The assay methods may also be of value in selecting or monitoring therapies for a disease.

Antibodies and autoantibodies can also serve as biological markers of other disease states or disease susceptibilities, of which rheumatoid arthritis, systemic lupus erythematous (SLE), primary biliary cirrhosis (PBC), autoimmune thyroiditis (eg Hashimoto's thyroiditis), autoimmune gastritis (eg pernicious anaemia), autoimmune adrenalitis (eg Addison's disease), autoimmune hypoparathyriodism, autoimmune diabetes (eg Type 1 diabetes), myasthenia gravis are but examples.

The present inventors have recognised that when assays based on detection of antibodies are used diagnostically or prognostically to assess the disease state, disease progression or disease susceptibility of an individual within a population, difficulties can arise in devising a standardised assay methodology appropriate for the whole population of subjects to be screened because the absolute amounts of antibody present vary dramatically from individual to individual. This can produce a high incidence of false negative results, for example amongst individuals having a low amount of antibody. Similarly there is a difficulty in scoring true positive results because the variation in absolute amounts of antibody from individual to individual means that it is difficult to set a threshold for a positive assay result that is appropriate for all individuals within the population screened.

The present inventors have determined that the performance and more specifically the clinical utility and reliability of assays based on detection of antibodies, particularly autoantibodies, as biological markers of disease can be improved dramatically by inclusion of an antigen titration step. By testing the sample suspected of containing antibodies against a series of different amounts of antigen and constructing a titration curve it is possible to reliably identify true positive screening results independently of the absolute amount of antibody present in the sample. Such an approach is contrary to prior art methods which titrate antigen merely to construct a calibration curve to allow identification of the most appropriate antigen concentration to be used for detecting antibodies in actual patient samples. In these methods only a single point measurement is proposed for actual diagnosis. Thus, these methods will not allow for variation in amounts of the antibody to be detected from individual to individual resulting in the incidence of false positives and false negatives. The present inventors have found that assay methods based on antigen titration exhibit greater specificity and sensitivity than measuring autoantibody reactivity at a single antigen concentration.

The inventors have further determined that assay methods which combine antigen titration with simultaneous titration of the test sample offer even greater advantages than methods based on antigen titration alone, particularly in the context of autoantibody detection. These so-called "cross-titration" methods form the subject matter of the present invention.

SUMMARY OF THE INVENTION

According to a first aspect of the invention there is provided a method of detecting a disease state or disease susceptibility in a mammalian subject, said method comprising detecting an antibody in a test sample, wherein the test sample comprises a bodily fluid from said mammalian subject and wherein said antibody is a biological marker of a disease state or disease susceptibility, which method comprises:
(a) preparing two or more different dilutions of said test sample and carrying out the following steps (i) and (ii) in respect of each test sample dilution:
  (i) contacting the test sample dilution with a plurality of different amounts of an antigen specific for said antibody,
  (ii) detecting the amount of specific binding between the antibody and the antigen for each amount of antigen used in step (i),
(b) plotting or calculating a separate curve of the amount of specific binding versus the amount of antigen for each test sample dilution used in step (a), and
(c) determining the presence or absence of said disease state or disease susceptibility based upon the amount of specific binding between said antibody and said antigen for each test sample dilution and amount of antigen tested.

According to a second aspect of the invention there is provided a method of detecting an antibody in a test sample comprising a bodily fluid from a mammalian subject wherein said antibody is a biological marker of a disease state or disease susceptibility, which method comprises:
(a) preparing two or more different dilutions of said test sample and carrying out the following steps (i) and (ii) in respect of each test sample dilution:
  (i) contacting the test sample dilution with a plurality of different amounts of an antigen specific for said antibody,
  (ii) detecting the amount of specific binding between the antibody and the antigen for each amount of antigen used in step (i),
(b) plotting or calculating a separate curve of the amount of specific binding versus the amount of antigen for each test sample dilution used in step (a), wherein the presence in the test sample of antibody reactive with the antigen used in the assay is indicated by a generally S shaped or sigmoid curve for at least two different dilutions of the test sample.

According to a third aspect of the invention there is provided a method of detecting an antibody in a test sample comprising a bodily fluid from a mammalian subject, wherein said antibody is directed to a foreign substance introduced into said mammalian subject, the method comprising:
which method comprises:
(a) preparing two or more different dilutions of said test sample and carrying out the following steps (i) and (ii) in respect of each test sample dilution:
  (i) contacting the test sample dilution with a plurality of different amounts of an antigen specific for said antibody,
  (ii) detecting the amount of specific binding between the antibody and the antigen for each amount of antigen used in step (i),
(b) plotting or calculating a separate curve of the amount of specific binding versus the amount of antigen for each test sample dilution used in step (a), and wherein the presence in the test sample of antibody reactive with the antigen used in the assay is indicated by a generally S shaped or sigmoid curve for at least two different dilutions of the test sample.

In all aspects of the invention the mammalian subject is preferably a human.

In all aspects of the invention the antibody may be an autoantibody.

In all aspects of the invention the method is preferably carried out in vitro on a test sample comprising a bodily fluid obtained or prepared from the mammalian subject.

In all aspects of the invention, step (a) of the assay will preferably involve contacting each and every test sample dilution with each and every amount of antigen used in the assay, such that all possible combinations of test sample dilutions and amounts of antigen are tested.

A particular feature of the invention in all its aspects is that the judgement as to whether the relevant antibody is or is not present in the test sample is based upon the amount of specific binding observed at each and every different combination of test sample dilution and antigen concentration tested, in other words the collective values, rather than just a reading at a single antigen concentration or for a single test sample dilution. Thus, the determination of the presence or absence of disease state or disease susceptibility or antibodies to a foreign substance in a patient sample can follow based directly on these collective values. In one embodiment, the judgement is made on the basis of the presence of a generally S-shaped or sigmoid curve when the amount of specific binding is plotted against the amount of antigen for at least two different dilutions of the test sample. As will be apparent from the Examples herein, the inventors have observed that the methods of the invention have higher sensitivity with at least equivalent specificity to methods of diagnosis or detection based upon antigen titration alone and reduce incidence of false positive and false negative determinations.

The present invention will now be further described. In the following passages different features of the various aspects of the invention are defined in more detail. Each feature so defined in connection with one aspect of the invention may be combined with features described in connection with any other aspect of the invention unless clearly indicated to the contrary. In particular, any feature indicated as being preferred or advantageous may be combined with any other feature or features indicated as being preferred or advantageous unless clearly indicated to the contrary.

BRIEF DESCRIPTION OF THE DRAWINGS

FIG. 2 illustrates an example of a titration plate layout used to perform Optimal Serum and Antigen Concentration (OS-AAC) assays according to example 3. Note—the dilutions of serum and antigen are shown on separate plates, whereas in practice the serum and antigen dilutions are added to corresponding wells in the same single plate.

FIGS. 3a and b show representative titration curves for detection of anti-p53 autoantibodies in serum from a primary breast cancer patient (FIG. 3a) or a normal control subject (FIG. 3b).

FIGS. 4a and b show representative titration curves for detection of anti-ECD6 autoantibodies (using ECD6 antigen) in serum from a primary breast cancer patient (FIG. 4a) or a normal control subject (FIG. 4b).

FIGS. 5a and b show representative titration curves for detection of anti-ECD6 autoantibodies (using ECD6 3' antigen) in serum from a primary breast cancer patient (FIG. 5a) or a normal control subject (FIG. 5b).

FIGS. 6a-c show representative titration curves for detection of anti-p53 autoantibodies or anti-ECD6 autoantibodies in serum from the same primary breast cancer patient using p53 antigen (FIG. 6a), ECD6 antigen (FIG. 6b) or ECD6 3' antigen (FIG. 6c).

FIGS. 7a-d show additional titration curves referenced in Example 3.

DETAILED DESCRIPTION OF THE INVENTION

Figure 1A:
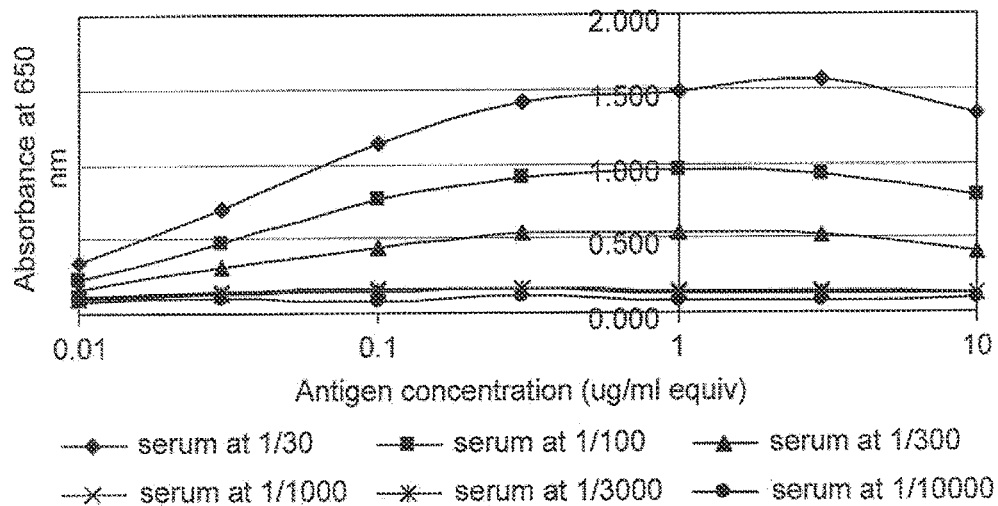
FIGS. 1 *a-h* show a series of cross titration curves for detection of autoantibodies against p53 (FIG. 1*a* to *d*) and c-myc (FIG. 1 *e* to *h*) in samples of serum taken from patients with breast cancer. In each experiment, six different dilutions of the patient serum were separately tested for specific binding against a titration series of varying amounts of recombinant p53 or c-myc antigen (serum dilution 1/10,000 is effectively a "no serum" control). For each antigen, separate curves of specific binding (expressed as absorbance at 650 nm) versus antigen concentration were plotted for each dilution of the patient serum.

In general terms the invention provides an immunoassay method for detecting an antibody which serves as a biological marker for a disease state or disease susceptibility, characterised in that two or more different dilutions of a sample to be tested for the presence of the antibody (the test sample) are each assayed for specific binding against different amounts of antigen specific for the antibody, and separate titration curves of the amount of antibody/antigen binding versus the amount of antigen tested are produced for each different dilution of the test sample. Put simply, the assay is based on cross-titration of both the test sample and the antigen used as a reagent in the immunoassay.

The general features of immunoassays, for example ELISA, radioimmunoassays and the like, are well known to those skilled in the art (see Immunoassay, E. Diamandis and T. Christopoulus, Academic Press, Inc., San Diego, Calif., 1996). Immunoassays for the detection of antibodies having a particular immunological specificity generally require the use of a reagent (antigen) that exhibits specific immunological reactivity with the antibody under test. Depending on the format of the assay this antigen may be immobilised on a solid support. A sample to be tested for the presence of the antibody is brought into contact with the antigen and if antibodies of the required immunological specificity are present in the sample they will immunologically react with the antigen to form antibody-antigen complexes which may then be detected or quantitatively measured.

The method of the invention is characterised in that two or more different dilutions of the sample to be tested for the presence of the antibody are each tested against a plurality of different amounts of antigen (also referred to herein as an antigen titration series). The assay must involve testing of at least two different dilutions of the test sample, but may involve testing of three, four, five, or from six to ten or even more different dilutions of the test sample. Each separate dilution of the test sample is tested against at least two, and preferably at least three, four, five, six, seven or more different amounts of the antigen. Typical assays may also include a negative control which does not contain any antigen and/or a negative test sample control, such as for example a 1/10,000 dilution of the test sample.

In this context the term "antigen" refers to a substance comprising at least one antigenic determinant or epitope capable of interacting specifically with the target antibody it is desired to detect, or any capture agent interacting specifically with the variable region or complementary determining regions of said antibody. The antigen will typically be a naturally occurring or synthetic biological macromolecule such as for example a protein or peptide, a polysaccharide or a nucleic acid and can include antibodies or fragments thereof such as anti-idiotype antibodies.

Skilled readers will appreciate that in the method of the invention the amount of antigenic determinants or epitopes available for binding to the target antibody is important for establishing a titration series. In many assay formats the amount of antigenic determinants or epitopes available for binding is directly correlated with the amount of antigen molecules present. However, in other embodiments, such as certain solid phase assay systems, the amount of exposed antigenic determinants or epitopes may not correlate directly with the amount of antigen but may depend on other factors, such as attachment to the solid surface. In these embodiments, references herein to "different amounts of antigen" in a titration series may be taken to refer to different amounts of the antigenic determinant or epitope.

The relative or absolute amount of specific binding between antibody (present in the test sample dilution) and antigen is determined for each different combination of test sample dilution and amount of antigen (antigenic determinant or epitope) tested. The results are then used to plot or calculate a series of curves of the (relative or absolute) amount of specific binding versus the amount of antigen for each amount of antigen tested, a separate curve being generated for each test sample dilution used in the assay. Typical results are illustrated, by way of example only, in the accompanying Figures for detection of a number of different antibodies. The presence in the test sample of antibody reactive with the antigen used in the assay is determined based upon the amount of specific binding observed at each antigen amount for each test sample dilution used in the assay and is usually indicated by the presence of a generally S-shaped or sigmoidal curve for at least two different test sample dilutions.

The absolute amounts of specific binding between antibody and antigen are generally not material, unless it is desired to produce a quantitative measurement. For a simple yes/no determination of the presence or absence of antibodies it is sufficient only that a curve of the correct shape is produced for at least two of the different test sample dilutions tested in the assay. If there is no variation in detectable binding over the different amounts of antigen tested for any of the test sample dilutions tested then this can be scored as an absence of a detectable amount of the antibody. In preferred embodiments of the invention the method is non-quantitative. It can thus give a yes/no determination of presence or absence of antibody using a dimensionless proportional relationship which is independent of signal strength.

A measure of the amount of antibody present in a particular sample can, if desired, be derived from the results of the cross-titration assay. In non-limiting embodiments involving clinical testing of a patient population, a cut-off for scoring a result in a particular patient as positive can be established in comparison to results obtained from a control group of normal subjects, for example a cut-off of mean+2 standard deviations of the normal group. Patient samples in which specific binding of antigen to target antibody (e.g. the value obtained after correcting for non-specific binding) falls above this cut-off for at least one antigen concentration may be scored as positive.

In other non-limiting embodiments of the invention a calibration system may be used in order to score unknown test samples as positive or negative. One such calibration system may be based on the use of known positive and negative control samples. Positive and negative control/calibrator samples may be analysed in parallel with the test sample(s) using the assay methodology of the invention. Unknown test samples are judged as positive or negative by comparison with the known positive and negative control samples used as calibrators.

The method of the invention is advantageous for use in clinical diagnostic, prognostic, predictive and/or monitoring assays where the absolute amounts of target antibody present can vary enormously from patient-to-patient. The inventors have observed that if such assays are based on detection of antibody binding using a single amount/concentration of test antigen, patient samples containing an amount of antibody which is at the very low or the very high end of the normal physiological range (of amount of antibody) across the population can be missed due to limitations of the assay methodology; samples with a low amount of antibody may be scored as false negative results, whereas those with very high levels of antibody may be off the scale for accurate detection within the chosen assay methodology.

In all embodiments of the invention the antibody detected using the cross titration assay methodology may be an autoantibody.

The cross titration assay method of the invention is particularly suitable for the detection of antibodies/autoantibodies as biological markers of disease state or susceptibility where there is considerable patient-to-patient variation both in the absolute amounts of antibody/autoantibody present in the patient, and in the specificity of the antibodies/autoantibodies, in particular the affinity of the antibody/autoantibody for it's target antigen. Autoantibody responses by their very nature can vary significantly from patient-to-patient, with variation occurring both in the absolute amounts of autoantibody present and in the specificity/affinity of the autoantibodies. The method of the invention can take account of this patient-to-patient variation, thus enabling a standard assay format (suitable for use in testing all individuals within a population) to be developed for any given antibody/autoantibody.

Interactions between autoantibodies and their target antigens are generally of low affinity but the strength of binding may vary from patient-to-patient, as outlined above. The method of the invention is particularly suited to detection of low affinity binding, as a positive result can be inferred from the shape of the titration curves generated for each test sample dilution used in the assay.

The method of the invention differs from assay methods based on antigen titration alone (i.e. assays which involve testing of a single test sample against an antigen titration series) in that it allows detection of signals produced by binding of low abundance and/or low affinity antibodies which might otherwise be masked by non-specific binding (of the antigen used in the assay) with non-target components in the test sample.

The inventors have observed considerable inter-antigen and also intra-antigen variation in the optimal test sample dilution required for optimal detection of target antibodies. Thus, the same patient test sample may have a first optimal dilution for detection of antibodies to a first antigen and a different optimal dilution for detection of antibodies to a second antigen derived from a different protein (inter-antigen variability). The "difference" in optimal test sample dilution for two antigens derived from different proteins may be several orders of magnitude. For example, a optimal dilution of a given test sample for detection of antibodies to a first antigen (protein A) might be 1:800, but the same test sample may require an optimal dilution of 1:50 for detection of antibodies to a second antigen (protein B). A similar effect can be observed when the antigens used are different fragments of the same protein, or a full length protein and a sub-fragment of this protein (intra-antigen variability). Thus, if the test sample is to be tested for reactivity against a panel of different antigens (which are derived from different proteins or fragments of a single protein or a combination thereof), the optimal dilution of test sample required for each antigen in the panel might be different. The method of the invention circumvents this problem by testing varying dilutions of the test sample against varying dilutions of each antigen in the panel each time the method is performed in a clinical setting. Thus, each antigen in the panel will automatically be tested at its "optimal" test sample dilution.

The inventors have also observed that inter-individual differences in the optimal test sample dilution for a particular antigen can occur. Thus, for any given antigen a test sample from a first subject may give an optimal result at a first test sample dilution (e.g. 1:100), whereas when a test sample from a second subject is tested using the same antigen a different dilution of the test sample may be optimal (e.g. 1:500). The method of the invention is able to take account of such patient-to-patient variation since for each antigen tested a range of test sample dilutions are tested against a range of antigen dilutions each time the assay is performed in a clinical setting. Thus, the method of the invention will always use the optimal test sample dilution for each antigen tested against each test sample.

The method of the invention also provides a safeguard against day-to-day variation in the performance of immunoassays used for detection of autoantibodies/antibodies for diagnostic, prognostic and/or monitoring (disease state or therapy) purposes. It is often observed that there can be considerable day-to-day variation in signal strength when carrying out immunoassays for detection of antibodies in samples comprising patient bodily fluids. Such variation might arise, for example, because of differences in the way in which the samples were obtained and stored prior to testing. Such factors make it difficult to score the results of clinical assays with certainty, for example on the basis of a simple threshold value of antibody/antigen binding. The present invention minimises the effects of such day-to-day variation since a positive result for the presence of antibody is clearly evident from the shape of the titration curves generated for each test sample dilution used in the assay, independent of signal strength.

A still further advantage of the method of the invention is that it allows dilution of the patient sample, yet still produces consistent results, and also that it will generally produce the same qualitative screening result (positive/negative) using bodily fluids from different sources in one individual (e.g. blood or serum versus ascites fluid or pleural effusion), even though the absolute concentration of antibodies may be different in the different fluids.

The method of the invention may be carried out in any suitable format which enables contact between multiple dilutions of a sample suspected of containing the antibody and multiple different amounts of an antigen. Conveniently, contact between different dilutions of the sample and different amounts of the antigen may take place in separate but parallel reaction chambers such as the wells of a microtitre plate.

Varying amounts of the antigen can be coated onto the wells of the microtitre plate by preparing serial dilutions from a stock of antigen across the wells of the microtitre plate. The stock of antigen may be of known or unknown concentration. Aliquots of prepared dilutions of the test sample may then be added to the wells of the plate, with the volume of the test sample kept constant in each well. The absolute amounts of antigen added to the wells of the microtitre plate may vary depending on such factors as the nature of the target antibody, the nature of the sample under test, dilutions of the test sample, etc, as will be appreciated by those skilled in the art. Generally the amounts of antigen and the dilutions of the test sample will be selected so as to produce a range of signal strength which falls within the acceptable detection range of the read-out chosen for detection of antibody/antigen binding in the method. Typical amounts and dilutions for testing of human serum samples suspected of containing anti-tumour marker autoantibodies are given in the accompanying examples. By way of example only, typical dilutions of the test sample may vary in the range of from 1/30 to 1/10,000 (or 1:50 to 1:1600). The tested amounts of antigen may typically vary in the range of from 0.01 µg/ml to 1 µg/ml, (or 0.16 nM to 160 nM) although this is not intended to be limiting.

As aforesaid, it is also possible to construct titration curves for two or more dilutions of the test sample starting with a single stock of antigen even when the absolute concentration of antigen in the stock is unknown. Provided that a same single stock solution is used and serially diluted in the same manner, it is possible to compare the results of separate titration assays for this antigen run on different starting test samples.

In a further embodiment of the assay different amounts of the antigen (antigenic determinants or epitopes) may be immobilised at discrete locations or reaction sites on a solid support. The entire support, or a discrete area of it comprising a sub-fraction of the reaction sites, may then be brought into contact with a dilution of the test sample and binding of antibody to antigen detected or measured separately at each of the discrete locations or reaction sites. Suitable solid supports also include microarrays, for example arrays wherein discrete sites or spots on the array comprise different amounts of the antigen. Microarrays can be prepared by immobilising different amounts of a particular antigen at discrete, resolvable reaction sites on the array. In other embodiments the actual amount of immobilised antigen molecules may be kept substantially constant but the size of the sites or spots on the array varied in order to alter the amount of binding epitope available, providing a titration series of sites or spots with different amounts of available binding epitope. In such embodiments the two-dimensional surface concentration of the binding epitope(s) on the antigen is important in preparing the titration series, rather then the absolute amount of antigen. Techniques for the preparation and interrogation of protein/peptide microarrays are generally known in the art.

It will be understood from the above discussion that in all of the embodiments of the invention variation in the amount of antigen may be achieved by changing the antigen or epitope density against which the test sample dilutions are tested, or by maintaining antigen or epitope density but increasing the surface area over which antigen is immobilized, or both.

Microarrays may be used to perform multiple assays for antibodies of different specificity in parallel. This can be done using arrays comprising multiple sets of different antigens, each set comprising a particular antigen at multiple different amounts or concentrations. The term "different antigens" encompasses antigens derived from different proteins or polypeptides (such as antigens derived from unrelated proteins encoded by different genes) and also antigens which are derived from different peptide epitopes of a single protein or polypeptide. A given microarray may include exclusively sets of different antigens derived from different proteins or polypeptides, or exclusively sets of different antigens derived from different peptide epitopes of a single protein or polypeptide, or a mixture of the two in any proportion. It should be noted that in all embodiments of the invention it is preferred that each individual antigen titration series comprise different amounts or concentrations of just one type of antigen and not mixtures of antigens.

As used herein the term "bodily fluid", when referring to the material to be tested for the presence of antibodies using the method of the invention, includes inter alia plasma, serum, whole blood, urine, sweat, lymph, faeces, cerebrospinal fluid, ascites, pleural effusion, seminal fluid, sputum, nipple aspirate, post-operative seroma or wound drainage fluid. As aforesaid, the methods of the invention are preferably carried out in vitro on dilutions of a test sample comprising bodily fluid removed from the test subject. The type of bodily fluid used may vary depending upon the identity of the antibody to be tested and the clinical situation in which the assay is used. In general, it is preferred to perform the assays on samples of serum or plasma. The test sample may include further components in addition to the bodily fluid, such as for example diluents, preservatives, stabilising agents, buffers etc. Dilutions of the test sample may be prepared using any suitable diluent. It will be appreciated by the skilled reader that the reason for preparing dilutions of the test sample is merely to produce a series of test samples each containing different absolute amounts of the target antibody to be detected in the immunoassay. It is not intended to exclude other means of obtaining "test samples" containing varying amounts of the target antibody. By way of example, a test sample removed from a patient could in fact be "concentrated" instead of diluted, for example using dialysis, in order to obtain a test sample containing a higher concentration of the antibody than occurs naturally. In other embodiments, such as when the bodily fluid removed from the patient is relatively dilute with respect to the target antibody, the bodily fluid might first be concentrated (e.g. by dialysis or similar techniques) to prepare a concentrated stock which is then used to prepare a series of dilutions for use in an assay according to the invention.

The term "antigen" is used herein in a broad sense to refer to any substance which exhibits specific immunological reactivity with a target antibody to be detected. Suitable antigens may include, but are not limited to, naturally occurring proteins, recombinant or synthetic proteins or polypeptides, synthetic peptides, peptide mimetics, etc, also polysaccharides and nucleic acids. Specifically, where "antigen" is used herein it is intended to encompass any capture agent, whether of human origin, mammalian origin or otherwise, capable of specific immunological interaction with the variable or complementary determining regions of the antibody to be detected. For example anti-idiotypic antibodies may be regarded as an antigen for this purpose as may antigens generated by phage display.

Certain antigens may comprise or be derived from proteins or polypeptides isolated from natural sources, including but not limited to proteins or polypeptides isolated from patient tissues or bodily fluids. In such embodiments the antigen may comprise substantially all of the naturally occurring protein, i.e. protein substantially in the form in which it is isolated from the natural source, or it may comprise a fragment of the naturally occurring protein. To be effective as an antigen in the method of the invention any such "fragment" must retain immunological reactivity with the antibodies for which it will be used to test. Suitable fragments might, for example, be prepared by chemical or enzymatic cleavage of the isolated protein.

Depending on the precise nature of the assay in which it will be used, the antigen may comprise a naturally occurring biomolecule (e.g. a protein, or fragment thereof), linked to one or more further molecules which impart some desirable characteristic not naturally present in the biomolecule. For example, the biomolecule (e.g. protein or polypeptide fragment) may be conjugated to a revealing label, such as for example a fluorescent label, coloured label, luminescent label, radiolabel or heavy metal such as colloidal gold. In other embodiments a protein or fragment may be expressed as a fusion protein. By way of example, fusion proteins may include a tag peptide at the N- or C-terminus to assist in purification of the recombinantly expressed antigen.

Depending on the format of the assay in which it is to be used the antigen may be immobilised on a solid support such as, for example, the wells of a microtitre plate, microarray beads or chips or magnetic beads. Immobilization may be effected via non-covalent adsorption or covalent attachment. Any suitable attachment means may be used provided this does not adversely affect the ability of the antigen to immunologically react with the target antibody to a significant extent.

The invention is not limited to solid phase assays, but also encompasses assays which, in whole or in part, are carried out in liquid phase, for example solution phase bead assays.

In one embodiment, antigens may be labelled with a ligand that would facilitate immobilisation, such as biotin. The antigen can then be diluted to a suitable titration range and then allowed to react with autoantibodies in patient samples in solution. The resulting immune complexes can then be immobilised to a solid support via a ligand-receptor interaction (e.g. biotin-streptavidin) and the remainder of the assay performed as described below.

To facilitate the production of biotinylated polypeptide antigens for use in the assay methods of the invention, cDNAs encoding a full length polypeptide antigen, a truncated version thereof or an antigenic fragment thereof may be expressed as a fusion protein labelled with a protein or polypeptide tag to which the biotin co-factor may be attached via an enzymatic reaction. Vectors for the production of recombinant biotinylated antigens are commercially available from a number of sources.

An additional advantage of the use of the cross-titration approach with biotinylated antigens is that the assay is able to distinguish between binding of the biotin component to antibiotin antibodies and true binding of the antigen to its cognate antibody. The inventors have observed that a significant number of the human population naturally produce anti-biotin antibodies which might lead to the production of false positive results in assays based on the use of biotinylated antigen.

As aforesaid, the "immunoassay" used to detect antibodies according to the invention may be based on standard techniques known in the art, with the exception that multiple amounts of antigen are used to create a titration series which can be reacted with multiple different dilutions of the chosen test sample. In a most preferred embodiment the immunoassay may be an ELISA. ELISAs are generally well known in the art. In a typical "indirect" ELISA an antigen having specificity for the antibodies under test is immobilised on a solid surface (e.g. the wells of a standard microtiter assay plate, or the surface of a microbead or a microarray) and a sample comprising bodily fluid to be tested for the presence of antibodies is brought into contact with the immobilised antigen. Any antibodies of the desired specificity present in the sample will bind to the immobilised antigen. The bound antibody/antigen complexes may then be detected using any suitable method. In one preferred embodiment a labelled secondary anti-human immunoglobulin antibody, which specifically recognises an epitope common to one or more classes of human immunoglobulins, is used to detect the antibody/antigen complexes. Typically the secondary antibody will be anti-IgG or anti-IgM. The secondary antibody is usually labelled with a detectable marker, typically an enzyme marker such as, for example, peroxidase or alkaline phosphatase, allowing quantitative detection by the addition of a substrate for the enzyme which generates a detectable product, for example a coloured, chemiluminescent or fluorescent product. Other types of detectable labels known in the art may be used.

The invention relates to a method of detecting antibodies that are biological markers of a disease state or disease susceptibility. This particular aspect of the invention preferably excludes assays designed to test for antibodies produced as a result of a vaccine challenge or immunisation protocol, other than vaccination with cancer markers. Therefore, assays according to this aspect of the invention preferably do not include assays designed to test for the presence of anti-viral or anti-bacterial antibodies following vaccination/immunisation.

In certain embodiments of the invention the antibody may be an autoantibody. As indicated above, the term "autoantibody" refers to a naturally occurring antibody directed to an antigen which an individual's immune system recognises as foreign even though that antigen actually originated in the individual. Autoantibodies include antibodies directed against altered forms of naturally occurring proteins produced by a diseased cell or during a disease process. The altered form of the protein originates in the individual but may be viewed by the individual's immune system as "non-self" and thus elicit an immune response in that individual in the form of autoantibodies immunologically specific to the altered protein. Such altered forms of a protein can include, for example, mutants having altered amino acid sequence, optionally accompanied by changes in secondary, tertiary or quaternary structure, truncated forms, splice variants, altered glycoforms etc. In other embodiments the autoantibody may be directed to a protein which is overexpressed in a disease state, for example as a result of gene amplification or abnormal transcriptional regulation. Overexpression of a protein which is not normally encountered by cells of the immune system in significant amounts can trigger an immune response leading to autoantibody production. In still further embodiments the autoantibody may be directed to a fetal form of a protein which becomes expressed in a disease state. If a fetal protein which is normally expressed only in early stages of development before the immune system is functional becomes expressed in a disease state, the fetal form may be recognised by the immune system as "foreign", triggering an immune response leading to autoantibody production.

In one embodiment the antibody may be an autoantibody specific for a tumour marker protein, and more particularly a "cancer-associated" anti-tumour autoantibody.

The term "cancer-associated" anti-tumour autoantibody refers to an autoantibody which is directed against an epitope present on forms of tumour marker proteins which are preferentially expressed in the cancer disease state. The presence of such autoantibodies is characteristic of the cancer disease state, or of pre-disposition to cancer in asymptomatic patients.

In preferred applications, the method of the invention will be used to detect the presence of cancer-associated anti-tumour autoantibodies in test samples derived from human subjects or patients (although the method may be used on test samples derived from other non-human mammals), and will most preferably take the form of an in vitro immunoassay, performed on two or more dilutions of a test sample comprising a sample of bodily fluid taken from the subject/patient. The sample of bodily fluid may be diluted in any suitable buffer and may be treated for long term storage or otherwise prior to testing.

In vitro immunoassays are non-invasive and can be repeated as often as is thought necessary to build up a profile of autoantibody production in a patient, either prior to the onset of disease, as in the screening of "at risk" individuals, or throughout the course of disease (discussed further below in relation to preferred applications of the method).

In particular, but non-limiting, embodiments the methods of the invention may comprise immunoassays to (simultaneously) detect two or more types of autoantibodies, each having specificity for different epitopes on the same or related tumour marker proteins (e.g. different isoforms or variants encoded by a single gene) or for epitopes on different tumour marker proteins (meaning proteins encoded by different genes). These methods will typically involve use of a panel of two or more sets of antigens, each set of antigens usually being derived from a different tumour marker protein (different in this context meaning proteins that are the products of different genes) although as noted above a set of antigens could also involve different epitopes on the same tumour marker protein. A "set" of antigens refers to a single antigen to be tested at different amounts/concentrations in the method of the invention. These methods, which may be hereinafter referred to as "panel assays", utilise a panel of two or more sets of antigens to monitor the overall immune response of an individual to a tumour or other carcinogenic/neoplastic change. These methods thus detect a "profile" of the immune response in a given individual, indicating which tumour markers elicit an immune response resulting in autoantibody production. The use of a panel of two or more antigens to monitor production of autoantibodies against two or more different tumour markers is generally more sensitive than the detection of autoantibodies to single markers and gives a much lower frequency of false negative results (see WO 99/58978 and WO 2004/044590, the contents of which are incorporated herein in their entirety by reference).

Therefore, in a non-limiting embodiment the invention provides a method of detecting two or more antibodies in a test sample comprising a bodily fluid from a mammalian subject wherein at least one of said antibodies is a biological marker of a disease state or disease susceptibility, which method comprises:

(a) preparing two or more different dilutions of said test sample and carrying out the following steps (i) and (ii) in respect of each test sample dilution:
  (i) contacting the test sample dilution with two or more sets of antigens, wherein each one of said sets of antigens is specific for one of said antibodies to be detected in the test sample and wherein each set of antigens comprises a plurality of different amounts of the same antigen,
  (ii) detecting the amount of specific binding between the antibody and the antigen for each amount of antigen in each set of antigens used in step (i), (b) plotting or calculating a separate curve of the amount of specific binding versus the amount of antigen for each test sample dilution with each set of antigens used in step (a), wherein the presence in the test sample of antibody reactive with any one of the sets of antigens used in the assay is indicated by a generally S shaped or sigmoid curve for at least two different dilutions of the test sample with that set of antigens.

a. In one embodiment of this method each of said two or more antibodies will be a biological marker of a disease state or disease susceptibility, however it is within the scope of the invention to combine a cross titration assay for a disease marker antigen with a cross titration assay for any other type of antibody, which may or may not be a disease marker, in the same test sample.

b. Either way the judgement as to whether the relevant antibodies are or are not present in the test sample is based upon the amount of specific binding observed at each of the different antigen concentrations in respect of each different antigen in the test, in other words the collective values for each antigen rather than a reading at a single concentration for each antigen. Thus, the determination of presence or absence of disease state or disease susceptibility based upon presence of two or more types of antibody in a patient sample can be based on these collective values for each antigen. Preferably, the judgement is made on the basis of the showing of a generally S-shaped or sigmoidal curve for at least two different test sample dilutions in respect of any or all of the antigens present in the test.

c. For the avoidance of doubt, assays based on the use of a single type of antigen to detect antibodies may be referred to herein as "single marker assays", whereas assays based on the use of a panel of two or more antigens are referred to as "panel assays".

d. In a preferred embodiment of the panel assay method at least one and preferable all of the antibodies detected in the assay are autoantibodies reactive with tumour marker proteins.

e. Cross titration assays according to the invention may be adapted for use in the detection of autoantibodies to essentially any tumour marker protein for which a suitable antigen may be prepared, as a single marker assay or as a component of a panel assay. In particular, the method may be adapted to detect/measure autoantibodies immunologically specific to any one or any combination of two or more of the following tumour marker proteins, by use of the corresponding antigens:

Epidermal growth factor receptor protein EGFR (Downward et al. (1984) *Nature.* 307: 521-527; Robertson et al. (2001) *Archives of Pathology and Laboratory Medicine* 126; 177-81);
MUC1 (Batra, S. K. et al. (1992) *Int. J. Pancreatology.* 12: 271-283);
Myc (c-myc) (Blackwood, E. M. et al. (1994) *Molecular Biology of the Cell* 5: 597-609);
p53 (Matlashewski, G. et al. (1984) *EMBO J.* 3: 3257-3262; Wolf, D. et al. (1985) *Mol. Cell. Biol.* 5: 1887-1893);
ras (or Ras) (Capella, G. et al. (1991) *Environ Health Perspectives.* 93: 125-131);
BRCA1 (Scully, R. et al. (1997) *PNAS* 94: 5605-10);
BRCA2 (Sharan, S. K. et al. (1997) *Nature.* 386: 804-810);
APC (Su, L. K. et al. (1993) *Cancer Res.* 53: 2728-2731; Munemitsu, S. et al. (1995) *PNAS* 92: 3046-50);
CA125 (Nouwen, E. J. et al. (1990) *Differentiation.* 45: 192-8; Norum L F, et al., *Tumour Biol.* 2001 July-August;

22(4):223-8; Perey L, et al., *Br J. Cancer.* 1990 October; 62(4):668-70; Devine P L, et al., *Anticancer Res.* 1992 May-June; 12(3):709-17);

PSA (Rosenberg, R. S. et al. (1998) *Biochem Biophys Res Commun.* 248: 935-939);

Carcinoembryonic antigen CEA (Duffy, M. J. (2001) *Clin Chem,* April 47(4):624-30);

CA19.9 (Haga, Y. et at (1989) *Clin Biochem* (1989) October 22(5): 363-8);

NY-ESO-1 (cancer/testis antigen; Chen, Y.-T. et al., *Proc. Nat. Acad. Sci.* 94: 1914-1918, 1997);

PSMA (prostate specific membrane antigen; Israeli, R. S. et al., *Cancer Res.* 53: 227-230, 1993);

PSCA (prostate stem cell antigen; Reiter, R. E. et al., *Proc. Nat. Acad. Sci.* 95: 1735-1740, 1998);

EpCam (epithelial cellular adhesion molecule; Szala, S. et al., *Proc. Nat. Acad. Sci.* 87: 3542-3546, 1990);

HER2-neu (also known as c-erbB2) (Coussens, L. et al., *Science* 230: 1132-1139, 1985);

EDC6, which is an alternative name for the extracellular domain of HER2.

CAGE (Jager D, et al., *Cancer Res.* 1999 Dec. 15; 59(24): 6197-204; Mashino K, et al., *Br J. Cancer.* 2001 Sep. 1; 85(5):713-20);

Cytokeratins (Moll R, et al., *Cell.* 1982 November; 31(1):11-24; Braun S, et al., N Engl J. Med. 2000; 342: 525-533). The term "cytokeratin" is used generically to refer to any member of the cytokeratin family for which the corresponding autoantibodies function as tumour markers. Preferred examples are cytokeratins 5/14, 8/18 (Kim M J, Ro J Y, Ahn S H, Kim H H, Kim S B, Gong G Hum Pathol. 2006 September; 37(9):1217-26. Epub 2006 Jul. 18); cytokeratins 7, 20 (Nang R, Gown A M, Barry T S, Wheeler D T, Yemelyanova A, Seidman J D, Ronnett B M. *Am J Surg Pathol.* 2006 September; 30(9):1130-1139); and cytokeratins 8/18/19 (Barak V, Goike H, Panaretakis K W, Einarsson R. *Clin Biochem.* 2004 July; 37(7):529-40).

Recoverin (Maeda A, et al., *Cancer Res.* 2000 Apr. 1; 60(7): 1914-20);

Kallikreins (Kim H, et al., *Br J Cancer* 2001; 84:643-650; Yousef G M, et al., *Tumor Biol* 2002; 23:185-192). The term "kallikrein" is used generically to refer to any member of the kallikrein family for which the corresponding autoantibodies function as tumour markers. Preferred examples are kallilreins 1 to 15 (KLK 1-15/Hk1-Hk15) (Obiezu C V, Diamandis E P. *Cancer Lett.* 2005 Jun. 16; 224(1):1-22; Diamandis E P, Yousef G M. *Clin Chem.* 2002 August; 48(8):1198-205), and in particular KLK 4-7 (Prezas P, Arlt M J, Viktorov P, Soosaipillai A, Holzscheiter L, Schmitt M, Talieri M, Diamandis E P, Kruger A, Magdolen V. *Biol Chem.* 2006 June; 387(6):807-11; Diamandis E P, Yousef G M, Luo L Y, Magklara A, Obiezu C V. The new human kallikrein gene family: implications in carcinogenesis. *Trends Endocrinol Metab.* 2000 March; 11(2):54-60. Review.);

Annexins (Hudelist G, et al., *Breast Cancer Res Treat.* 2004 August; 86(3):281-91; Gerke, V. & Moss, S. E. Physiological Reviews 2002 82: 331-371). The term "annexin" is used generically to refer to any member of the annexin family for which the corresponding autoantibodies function as tumour markers. Preferred examples are annexins 1 and 2 (Pedrero, J. M. G., Fernandez, M. P., Morgan, O., Zapatero, A. H., Gonzalez, M. V., Nieto, C. S. & Rodrigo, J. P. *American Journal of Pathology* 2004 164(1): 73-79; Brichory, F. M., Misek, D. E., Yim, A., Krause, M. C., Giordano, T. J., Beer, D. G., Hanash, S. M. 2001 *Medical Sciences* 98(17): 9824-9829) and annexin XI-A (Fernández-Madrid, F., Tang, N., Alansari, H., Granda, J. L., Tait, L., Amirikia, K. C., Moroianu, M., Wang, X. & Karvonen, R. L. *Cancer Research* 2004 64: 5089-5096);

α-fetoprotein (AFP) (Stiller D, et al., *Acta Histochem Suppl.* 1986; 33:225-31);

GRP78 (Block T M, et al., *Proc Natl Acad Sci USA*. 2005 Jan. 18; 102(3):779-84; Hsu W M, et al., *Int J. Cancer.* 2005 Mar. 1; 113(6):920-7);

Mammaglobin (Zehentner B K, et al., *Clin Chem.* 2004 November; 50(11):2069-76; Zehentner B K, Carter D. *Clin Biochem.* 2004 April; 37(4):249-57);

raf (Callans L S. et al., Ann Surg Oncol. 1995 January; 2(1): 38-42; Pratt M A, et al., *Mol Cell Biochem.* 1998 December; 189 (1-2):119-25);

beta-human chorionic gonadotropin b-HCG (Ayala A R, et al., *Am J Reprod Immunol.* 1983 April-May; 3(3): 149-51; Gregory J J Jr, et al., *Drugs.* 1999 April; 57(4):463-7);

4-5 antigen (Krause P, et al., *J Immunol Methods.* 2003 December; 283 (1-2):261-7);

NY-BR-1 (Jage D, Stockert E, Gure A O, Scenlan M J, Karbach J, Jage E, Knuth A, Old L J, Chen Y T. (2001) Identification of a tissue-specific putative transcription factor in breast tissue by serological screening of a breast cancer library. *Cancer Res* 61 (5): 2055-61);

Livin (Kasof G M, Gomes B C (2001) Livin, a novel inhibitor of apoptosis protein family. *J Biol Chem,* 276 (5): 3238-46);

Survivin (Ambrosini G, Adida C, Alfieri D C (1997) A novel anti-apoptois gene, survivin, expressed in cancer and lymphoma. *Nature Med,* 3 (8): 917-21);

MUC2 (glycoprotein)

Griffiths B, Matthews D J, West L, Attwood J, Povey S, Swallow D M, Gum J R Kim Y S (1990) Assignment of the polymorphic intestinal mucin gene MUC2 to chromosome-11p15. *Ann Hum Genet,* 54: 277-85.

Endostatin (Standker L, Schrader M, Kanse S M, Jurgens M, Forssmann W G, Preissner K T (1997) Isolation and characterisation of the circulating form of human endostatin. *FEBS Lett,* 420 (2-3): 129-33;

Bcl-2 (Tsujimoto Y, Croce C M (1986) Analysis of the structure, transcripts, and protein products of Bcl-2, the gene involved in human follicular lymphoma. *PNAS USA,* 83 (14): 5214-8);

BIRC7 (Wu Hy, Ma Yh, Zhu Yk, Shen Y, Gu C M, Ye Z Y, Lin H L (2006) The expression of BIRC7 protein and mRNA in non-Hodgkin's lymphoma. *Leukemia & Lymphoma* 47 (6): 1110-6);

Heat shock proteins (the term heat shock proteins is used generically to refer to any heat shock proteins for which the corresponding autoantibodies function as tumour markers) including but not exclusively: HSP70 (Tauchi K, Tsutsumi Y, Hori S, Yoshimura S, Osamura Ry, Watanabe K (1991) Expression of heat shock protein-70 and c-myc protein in human breast-cancer—an immunohistochemical study. *Jap J Clin Oncol,* 21 (4): 256-63); HSP27 (Differential expression of alphaB-crystallin and Hsp27-1 in anaplastic thyroid carcinomas because of tumor-specific alphaB-crystallin gene (CRYAB) silencing. Mineva I, Gartner W, Hauser P, Kainz A, Loffler M, Wolf G, Oberbauer R, Weissel M, Wagner L. *Cell Stress Chaperones.* 2005 Autumn; 10(3):171-84); and CRYAB (Seitz S, Korsching E, Weimer J, Jacobsen A, Arnold N, Meindl A, Arnold W, Gustavus D, Klebig C, Petersen I, Scherneck S. *Genes Chromosomes Cancer.* 2006 June; 45 (6):612-27).

No55 (Fossa A, Siebert R, Aasheim H C, Maelandsmo G M, Berner A, Fossa S D, Smeland E B Gaudernack G (2000)

Identification of a nucleolar protein No55 as a tumour-associated auto-antigen in patients with prostate cancer. *Br J Cancer* 83 (6): 743-9).

Urokinas-type Plasminogen Activator (uPA) (Booyse F M, Osikowicz G, Feder S, Scheinbuks J (1984) Isolation and characterisation of a urokinase-type plasminogen activator (MR=54,000) from cultures human epithelial cells indistinguishable from urinary urokinase. *J Biol Chem* 259 (11): 7198-205);

Tetranectin (plasminogen binding protein) (Clemmensen I, Petersen L C, Kluft C (1986) Purification and characterization of a novel, Oligomeric, Plasminogen Kringle 4 binding-protein from human plasma—Tetranectin. *Eur J Biochem* 156 (2): 237-333);

Prolactin (Riddle O, bates R W, Dykshorn S W (1933) The preparation, identification and assey of prolactin—A hormone of the anterior pituitary. *Am J Physiol* 105 (1): 191-216);

Osteopontin (Butler W T, Martin T J, Raisz L G, Slavkin H C Termine J D, Rodan G A, Veis A (1988) Osteopontin—Structure and biological activity. *CBA Foundation Symposia* 136: 203-206; Kiefer M C, Bauer D M, Barr P J (1989) The CDNA and derived amino-acid sequence for human Osteopontin. *Nucleic Acids Res* 17 (8): 3306-3306);

Human Epididymis Specific Protein (HE4) Kirchoff C, Habben I, Ivell R, Krull N (1991) A major human epididymis-specific cDNA encodes a protein with sequence homology to extracellular proteinase-inhibitors. *Biology of Reproduction* 45 (2): 350-357);

Tumour Asscociated Trypsin Inhibitor (TATI) (Huhtala M L, Kahanpaa K, Seppala M, Halila H, Stenman U H (1983) Excretion of a tumour associated trypsin-inhibitor (TATI) in urine of patients with Gynecological Malignancy. *Int J Cancer* 31 (6): 711-714, 1983;

Inhibin (Chari S, Hopkinson C R N, Fritze E, Sturm G, Hirschhauser C. (1977) Partial-Purification of Inhibin from Human Testicular Extracts. *ACTA Endocrinologia* 85 (Suppl 212): 215-219);

Vimentin (Yang Y C, Li X, Chen W. *Acta Biochim Biophys Sin* (Shanghai). 2006 September; 38(9):602-10);

Cox-1 and Cox-2 (Xu Z, Choudhary S, Voznesensky O, Mehrotra M, Woodard M, Hansen M, Herschman H, Pilbeam C. Cancer Res. 2006 Jul. 1; 66(13):6657-64; Cervello M, Montalto G. World *J. Gastroenterol.* 2006 Aug. 28; 12(28):5113-5121).

It be will appreciated that the invention is not intended to be limited to the detection of autoantibodies to the specific tumour markers listed above by way of example only.

Assay methods according to the invention based on detection of anti tumour-marker autoantibodies (in single marker or panel assay form) may be employed in a variety of different clinical situations. In particular, the method may be used in the detection or diagnosis of cancer in symptomatic or asymptomatic human subjects, in assessing the prognosis of a patient diagnosed with cancer, in predicting response to therapy, in monitoring the progress of cancer or other neoplastic disease in a patient, in detecting early neoplastic or early carcinogenic change in an asymptomatic human subject, in screening a population of asymptomatic human subjects in order either to identify those subjects who are at increased risk of developing cancer or to diagnose the presence of cancer, in predicting the response of a cancer patient to anti-cancer treatment (e.g. vaccination, anti-growth factor or signal transduction therapies, radiotherapy, endocrine therapy, human antibody therapy, chemotherapy), in monitoring the response of a cancer patient to anti-cancer treatment (e.g. vaccination, anti-growth factor or signal transduction therapies, radiotherapy, endocrine therapy, human antibody therapy chemotherapy), in the detection of recurrent disease in a patient previously diagnosed as having cancer who has undergone anti-cancer treatment to reduce the amount of cancer present, or in the selection of an anti-cancer therapy (e.g. vaccine, anti-growth factor or signal transduction therapies, radiotherapy, endocrine therapy, human antibody treatment chemotherapy), for use in a particular patient.

The inventors have generally observed that levels of cancer-associated autoantibodies show a positive correlation with disease state (see also WO 99/58979, the contents of which are incorporated herein by reference). Hence, when the method of the invention is used in clinical applications increased levels of anti-tumour marker autoantibodies, as compared to suitable controls, are generally taken as an indication of the cancer disease state, unless otherwise indicated herein.

When the immunoassays are used in the diagnosis of cancer in a human individual (either symptomatic or asymptomatic for cancer), the presence of an elevated level of autoantibodies, as compared to "normal" control individuals, is usually taken as an indication that the individual has cancer. The "normal" control individuals will preferably be age-matched controls not having any diagnosis of cancer based on clinical, imaging and/or biochemical criteria. A particularly useful application of the method is in testing of human subjects who already manifest cancer symptoms (e.g. based on clinical, imaging and/or biochemical criteria) in order to assist in making or confirming a diagnosis of cancer.

When the immunoassays are used in predicting the response of a cancer patient to anti-cancer treatment (e.g. vaccination, anti-growth factor or signal transduction therapies, radiotherapy, endocrine therapy, human antibody therapy, chemotherapy), the presence of an elevated level of autoantibodies, as compared to "normal" control individuals, may be taken as an indication of whether or not the individual is likely to respond to the anti-cancer treatment. The "normal" control individuals will preferably be age-matched controls not having any diagnosis of cancer based on clinical, imaging and/or biochemical criteria. For each of the treatments listed above, a relationship between the level of autoantibodies compared to controls and likely success of treatment can be established by observation of the outcome of such treatment in patients whose autoantibody status is monitored throughout treatment. The previously established relationship may then be used to predict the likelihood success for each treatment in a given patient based on assessment of autoantibody status.

When the immunoassays are used in monitoring the progress of cancer or other neoplastic disease in a patient, the presence of an elevated level of autoantibodies, as compared to a "normal control", is taken as an indication of the presence of cancer in the patient. The "normal control" may be levels of autoantibodies present in control individuals, preferably age-matched, not having any diagnosis of cancer based on clinical, imaging and/or biochemical criteria. Alternatively, the "normal control" may be a "base-line" level established for the particular patient under test. The "base-line" level may be, for example, the level of autoantibodies present when either a first diagnosis of cancer or a diagnosis of recurrent cancer was made. Any increase above the base-line level would be taken as an indication that the amount of cancer present in the patient has increased, whereas any decrease below the base-line would be taken as an indication that the amount of cancer present in the patient has decreased. The "base-line" value may also be, for example, the level before a new treatment is commenced. A change in the level of autoantibodies would be taken as an indication of the effectiveness of the therapy. The direction of the "change" (i.e. increase vs decrease) indicating a positive response to treatment will be dependent upon the precise nature of the treatment. For any given treatment the direction of the "change" in autoantibody levels indicating a positive result may be readily determined, for example by monitoring autoantibody levels in comparison to other clinical or biochemical indicators of response to the treatment.

When the immunoassays are used in screening a population of asymptomatic human subjects this may be to identify those subjects who are at increased risk of developing cancer, individuals having an elevated level of autoantibodies, as compared to "normal" control individuals, are identified as being "at risk" of developing cancer. The "normal" control individuals will preferably be age-matched controls not identified as having any predisposition to developing cancer or any significant elevated risk of developing cancer. An exception to this may be where age itself is a major risk factor.

When the immunoassays are used in screening a population of asymptomatic human subjects this may be to diagnose cancer in those subjects who have already developed a cancer, individuals having an elevated level of autoantibodies as compared to "normal" control individuals being scored as having cancer or some form of neoplastic change. The "normal" control individuals will preferably be age-matched controls not identified as having any predisposition to developing cancer or any significant elevated risk of developing cancer. An exception to this may be where age itself is a major risk factor. Alternatively, the "normal control" may be a "base-line" level established for the particular patient under test. The "base-line" level may be, for example, the level of autoantibodies present when the patient was first tested and found to have levels not elevated above a "normal control" population. Any increase thereafter against this baseline measurement would be taken as an indication of the presence of cancer in that individual. Thus the individual could through such a baseline test become their own control for future autoantibody measurement.

When the immunoassays are used in monitoring the response of a cancer patient to anti-cancer treatment (e.g. vaccination, anti-growth factor or signal transduction therapies, radiotherapy, endocrine therapy, human antibody therapy, chemotherapy), the presence of an altered level of autoantibodies after treatment is taken as an indication that the patient has responded positively to the treatment. A baseline level of autoantibodies taken before treatment is commenced may be used for comparison purposes in order to determine whether treatment results in an increase or decrease in autoantibody levels. A change in the level of autoantibodies would be taken as an indication of the effectiveness of the therapy. The direction of the "change" (i.e. increase vs decrease) indicating a positive response to treatment will be dependent upon the precise nature of the treatment. For any given treatment the direction of the "change" in autoantibody levels indicating a positive result may be readily determined, for example by monitoring autoantibody levels in comparison to other clinical or biochemical indicators of response to the treatment.

The method of the invention may used in predicting and/or monitoring response of an individual to essentially any known anti-cancer treatment. This includes, for example human antibody therapy wherein monoclonal or polyclonal antibodies are infused into the patient, a non-limiting specific example being treatment with the anti-growth factor antibody Herceptin™ (Baselga, J., D. Tripathy et al., *J Clin Oncol.*, 14(3), 737-744, 1996). The presence of a natural autoantibody response may enhance or inhibit the effectiveness of treatment with artificially infused therapeutic antibodies. Using the method of the invention it is possible to correlate response to any anti-cancer treatment, including antibody therapy, with natural levels of autoantibodies prior to and over the course of the treatment in any patient or group of patients. This knowledge may then in turn be used to predict how other patients (or the same patient in the case of repeated treatment) will respond to the same treatment.

When the immunoassays are used in detection of recurrent disease, the presence of an increased level of autoantibodies in the patient, as compared to a "normal control", is taken as an indication that disease has recurred. The "normal control" may be levels of autoantibodies present in control individuals, preferably age-matched not having any diagnosis of cancer based on clinical, imaging and/or biochemical criteria. Alternatively, the "normal control" may be a "base-line" level established for the particular patient under test. The "base-line" level may be, for example, the level of autoantibodies present during a period of remission from disease based on clinical, imaging and/or biochemical criteria.

The assay method of the invention may be applied in the detection of many different types of cancer, of which examples are breast, bladder, colorectal, prostate, lung, pancreatic and ovarian cancers. The assays may complement existing methods of screening and surveillance. For example, in the case of primary breast cancer immunoassays for autoantibodies could be used to alert clinicians to biopsy small lesions on mammograms which radiographically do not appear suspicious or to carry out breast imaging or to repeat imaging earlier than planned. In the clinic, the assay methods of the invention are expected to be more objective and reproducible compared to current imaging techniques (i.e. mammography and ultrasound), the success of which can be operator-dependent.

"Panel assays" may be tailored having regard to the particular clinical application. A panel of antigens for detection of autoantibodies to at least p53 and HER2-neu (c-erbB2) is particularly useful for many types of cancer and can optionally be supplemented with other markers having a known association with the particular cancer, or a stage of the particular cancer, to be detected. For example for breast cancer the panel might additionally include MUC 1 and/or c-myc and/or BRCA1 and/or BRCA2 and/or PSA and/or mammaglobin and/or EpCam and/or EGFR and/or cytokeratins and/or NY-ESO-1 and/or NY-BR-1 and/or annexin 11A and/or survivin whereas for bladder cancer the panel might optionally include MUC 1 and/or c-myc, for colorectal cancer ras and/or APC and/or MUC2, for prostate cancer PSA and/or BRCA 1 and/or BRCA2 and/or p62, for ovarian cancer BRCA1 and/or BRCA2 and/or CA125 and/or beta-HCG and/or kallikreins and/or APC and for lung cancer livin and/or survivin and/or EpCam and/or recoverin and/or cytokeratins and/or l-myc and or CEA and/or MUC 1 and/or recoverin, for hepatocellular cancer AFP and/or beta HCG and/or gp78 and/or p62 and/or survivin. There are other preferred embodiments in which p53 or HER2-neu are not necessarily essential.

In the case of breast cancer suitable panels could be selected from the following: p53 and MUC 1 with optional HER2-neu and/or c-myc, and/or BRCA1 and/or BRCA2 and/or PSA and/or NY-ESO-1 and/or NY-BR-1 and/or EpCam and/or mammaglobin and/or survivin and/or annexin 11A and/or cytokeratins and/or EpCam;

p53 and c-myc with optional HER2-neu and/or MUC1 and/or BRCA1 and/or BRCA2 and/or PSA and/or NY-ESO-1 and/or NY-BR-1 and/or EpCam and/or mammaglobin and/or survivin and/or annexin 11A and/or cytokeratins and/or EpCam;
p53 and BRCA1 with optional c-erB2 and/or MUC 1 and/or c-myc and/or BRCA2 and/or PSA and/or NY-ESO-1 and/or NY-BR-1 and/or EpCam and/or mammaglobin and/or survivin and/or annexin 11A and/or cytokeratins and/or EpCam;
p53 and BRCA2 with optional HER2-neu and/or MUC 1 and/or c-myc and/or BRCA1 and/or PSA and/or NY-ESO-1 and/or NY-BR-1 and/or EpCam and/or mammaglobin and/or survivin and/or annexin 11A and/or cytokeratins and/or EpCam;
HER2-neu and MUC 1 with optional p53 and/or c-myc, and/or BRCA1 and/or BRCA2 and/or PSA and/or NY-ESO-1 and/or NY-BR-1 and/or EpCam and/or mammaglobin and/or survivin and/or annexin 11A and/or cytokeratins and/or EpCam;
HER2-neu and c-myc with optional p53 and/or MUC1 and/or BRCA1 and/or BRCA2 and/or PSA and/or NY-ESO-1 and/or NY-BR-1 and/or EpCam and/or mammaglobin and/or survivin and/or annexin 11A and/or cytokeratins and/or EpCam;
HER2-neu and BRCA1 with optional p53 and/or MUC 1 and/or c-myc and/or BRCA2 and/or PSA and/or NY-ESO-1 and/or NY-BR-1 and/or EpCam and/or mammaglobin and/or survivin and/or annexin 11A and/or cytokeratins and/or EpCam;
HER2-neu and BRCA2 with optional p53 and/or MUC 1 and/or c-myc and/or BRCA1 and/or PSA and/or NY-ESO-1 and/or NY-BR-1 and/or EpCam and/or mammaglobin and/or survivin and/or annexin 11A and/or cytokeratins and/or EpCam.
Such panels might also include p53 and/or c-myc and/or NY-ESO-1 and/or BRCA2.

In the case of colorectal cancer suitable panels could be selected for example from the following:
p53 and ras with optional HER2-neu and/or APC and/or MUC 2;
p53 and APC with optional HER2-neu and/or Ras and/or MUC2;
Ras and APC with optional p53 and/or HER2-neu and/or MUC2
Such panels might also include CEA and/or CA19-9.

In the case of prostate cancer suitable panels could be selected for example from the following:
p53 and PSA with optional BRCA1 and/or BRCA2 and/or HER2-neu and/or p62;
HER2-neu and PSA with optional p53 and/or BRCA1 and/or BRCA2 and/or p62.
Such panels might also include PSMA and/or PSCA and/or kallikreins.

In the case of ovarian cancer suitable panels could be selected for example from the following:
p53 and CA125 with optional HER2-neu and/or BRCA1 and/or BRCA2 and/or APC;
HER2-neu and CA125 with optional p53 and/or BRCA1 and/or BRCA2 and/or APC.
Such panels might also include annexins and/or CAGE and/or 4-5.

In the case of lung cancer suitable panels may be selected from:
p53 and NY-ESO-1, optionally with further markers;
HER2, annexins, livin, survivin, recoverin, MUC 1, c-myc, 1-myc, CEA, beta HCG, CAGE and 4-5.

Where the method of the invention is used to perform a "panel assay" based on two or more tumour marker antigens derived from different proteins, at least one of the antigens in the panel must be tested in a cross titration assay according to the invention, based on testing of two or more dilutions of the test sample against multiple different amounts of the antigen to form a series of titration curves, one for each test sample dilution used. Preferably each of the antigens forming the panel is tested according to the cross titration assay of the invention and a series of titration curves plotted/calculated for each individual antigen in the panel.

The invention also contemplates that a cross titration assay for detection of at least one anti-tumour marker antibody may be used in combination with an assay designed to detect at least one tumour marker protein (which may be related or unrelated to the antigen used in the cross titration assay) in the same patient sample. Thus assays for anti-tumour marker autoantibodies and assays for tumour marker proteins may be performed in parallel on a single patient sample.

In a further embodiment, the immunoassay method of the invention may be used in the selection of an anti-cancer vaccine for use in a particular patient. In this embodiment a sample of bodily fluid taken from the patient is tested using a panel of two or more antigens, each corresponding to a different tumour marker protein, in order to determine the relative strength of the patient's immune response to each of the different tumour marker proteins. The "strength of immune response" to a given tumour marker protein or proteins is indicated by the presence and/or the amount of cancer-associated autoantibodies specific to that tumour marker protein detected using the immunoassay; where autoantibodies are quantified, the greater the level of cancer-associated autoantibodies, the stronger the immune response. The tumour marker protein or proteins identified as eliciting the strongest immune response or strong responses in the patient (i.e. the highest level of autoantibodies) is or are then selected to form the basis of an anti-cancer vaccine for use in the patient.

The utility of the method of the invention is not limited to detection of anti-tumour autoantibodies, although the assay is particularly useful for this purpose. Cancer is just one example of a disease wherein detection of autoantibodies may be used as a biological marker for disease state/disease susceptibility. The inventors have shown that substantial advantages are gained by the use of a cross titration approach to detect autoantibodies in patient samples. It is therefore reasonable to conclude that similar advantages will be gained by the use of the cross titration approach to detect autoantibodies that are biological markers for diseases other than cancer. The method is therefore applicable to detection of any autoantibody which serves as a biological marker for a disease state or disease susceptibility, in any disease which has been shown (or can be shown) to be associated with autoantibody production.

Other applications of the method of the invention include, but are not limited to, detection of autoantibodies that are biological markers of autoimmune disease, such as for example rheumatoid arthritis, systemic lupus erythematous (SLE), primary biliary cirrhosis (PBC), autoimmune thyroiditis (e.g. Hashimoto's thyroiditis), autoimmune gastritis (e.g. pernicious anaemia), autoimmune adrenalitis (e.g. Addison's disease), autoimmune hypoparathyriodism, autoimmune diabetes (e.g. Type 1 diabetes) or myasthenia gravis and screening of patient samples for kidney or hepatic disease leading to insufficiency or failure of either organ, and for screening of patient samples post-transplantation to detect the presence of antibodies directed against either the diseased tissue (which has been left in-situ post-transplantation) or against the transplanted tissue.

In a further aspect the invention provides a method of detecting an antibody in a test sample comprising a bodily fluid from a mammalian subject, wherein said antibody is directed to a foreign substance introduced into said mammalian subject, the method comprising:

(a) separately contacting two or more different dilutions of said test sample with a plurality of different amounts of an antigen specific for said antibody,
(b) detecting the amount of specific binding between the antibody and the antigen for each combination of test sample and antigen used in step (a),
(c) plotting or calculating a separate curve of the amount of specific binding versus the amount of antigen for each dilution of test sample used in step (a), wherein the presence in the test sample of antibody reactive with the antigen used in the assay is indicated by a generally S shaped or sigmoid curve for at least two different concentrations of the test sample.

In this aspect of the invention the cross titration methodology may be used to evaluate the immune response of a mammalian subject, and preferably a human subject, to any foreign substance introduced into said subject.

In one embodiment the foreign substance may be a therapeutic agent, such as for example a drug or prodrug, human antibody therapy or vaccine. The method of the invention may be used to assess whether administration of a therapeutic agent to a patient triggers an immune response leading to the production of antibodies specific for an epitope on the therapeutic agent, or a component of a delivery vehicle, excipient, carrier etc. administered with the therapeutic agent.

The antigens used in this embodiment of the invention may be synthetic or naturally occurring.

The precise nature of the therapeutic agent is not limiting to the invention. In non-limiting embodiments the method of the invention may be used to assess immune response to synthetic small molecules, naturally occurring substances, naturally occurring or synthetically produced biological agents, or any combination of two or more of the foregoing, optionally in combination with excipients, carriers or delivery vehicles.

In one useful embodiment the method of the invention may be used to assess the immune response to a non-target portion of a therapeutic agent or vaccine. By "non-target" portion is meant a component part of the administered therapeutic agent or vaccine which, in the case of a therapeutic agent, does not contribute directly to therapeutic activity or, in the case of a vaccine, is not intended to elicit production of antibodies in the host. The non-target portion may be present, for example, to facilitate purification of the therapeutic agent or vaccine or may be designed to assist with delivery, uptake or targeting of the therapeutic agent/vaccine. Examples of such "non-target" portions include, but are not limited to, linkers or markers commonly attached to recombinantly expressed polypeptides such as biotin labels, histidine tags etc.

In another embodiment of this aspect of the invention, the foreign substance may be an infectious agent, such as fungus, bacteria, virus or parasite.

The invention will be further understood with reference to the following non-limiting experimental examples:

Example 1

General Protocol for Optimal Serum and Antigen Concentration (OSAAC) Titration of Antigen in an Autoantibody Assay Samples of tumour marker antigens may be prepared by recombinant expression, following analogous methods to those described in WO 99/58978.

Briefly, cDNAs encoding the marker antigens of interest were cloned into the pET21 vector (Invitrogen) which has been modified to encode a biotin tag and a 6×histidine tag to aid in purification of the expressed protein. The resulting clones are grown in a suitable bacterial host cell (in inclusion bodies), the bacteria lysed and denatured and the expressed antigens recovered via Nickel chelate affinity columns (Hi-trap, commercially available from Amersham, following manufacturer's protocol). The expressed antigens were renatured by dialysis in appropriate buffer and the yield of expressed protein assessed by SDS-PAGE, western blot and ELISA and quantitated prior to storage. Unless otherwise stated, all antigens used in the following examples were prepared by recombinant expression from the modified pET21 vector and were therefore expressed as fusion proteins comprising an N-terminal biotinylation tag (derived from pET21) and a C-terminal His tag.

GenBank accession numbers for a number of marker cDNAs (or the encoded proteins) are as follows:

P53: B003596 c-myc: V00568

HER2 (erbB-2) isoform a: NP_004439

1. Antigens were diluted to appropriate concentrations in 0.1 M carbonate buffer then diluted serially to form a semi-log titration range (see table 1). Antigen dilutions were dispensed at 50 µl/well into the rows of a Falcon micotitre plate according to plate layout using a Tecan Evolyzer robotic pipetting station. Plates were covered and stored at 4° C. for 48 h.

2. Plates were washed once in PBS+0.1% tween 20 using an automated plate washer then tapped dry on tissue paper.

3. Plates were blocked with high salt incubation buffer (HSB, PBS+0.5M NaCl+0.1% casein) at 200 µl/well for 90 mins (store covered at 4° C.).

4. During blocking incubation, serum samples were defrosted, vortexed and serially diluted in a semi log series from 1/30 to 1/10,000 in HSB at room temperature in tubes.

5. Plates were emptied and tapped dry on tissue paper. Diluted serum samples were dispensed at 50 µl/well into all wells of the microtitre plate using an electronic multi-channel pipette to form a semi-log titration range (see table 1). Plates covered and incubated for 90 mins at room temp with shaking.

6. Wash step: Plates were washed three times in PBS+0.1% tween 20 using an automated plate washer then tapped dry on tissue paper.

7. Horseradish peroxidase conjugated rabbit anti-human Ig (Jackson, 1/10,000 in HSB) was dispensed at 50 µl/well into all wells of the microtitre plate. HRP-conjugated rabbit anti-mouse Ig (1/1000 in HSB) was dispensed into control wells containing anti-antigen antibody. Plates were then incubated at room temp for 1 hour with shaking.

8. Plates were washed as in step 6.

9. Pre-prepared TMB substrate was added at 50 µl/well and plate incubated on bench for 10 min. Plates were gently tapped to mix.

10. Optical density of wells was determined at 650 nm using a standard plate reader protocol.

TABLE 1

| Standard Plate Layouts | | | | | | | | | | | |
|---|---|---|---|---|---|---|---|---|---|---|---|
| 1 | 2 | 3 | 4 | 5 | 6 | 7 | 8 | 9 | 10 | 11 | 12 |
| A | antigen 10 µg/ml | | antigen 10 µg/ml | | antigen 10 µg/ml | | antigen 10 µg/ml | | antigen 10 µg/ml | | antigen 10 µg/ml |
| | Serum at 1 in 30 | | Serum at 1 in 100 | | Serum at 1 in 300 | | Serum at 1 in 1000 | | Serum at 1 in 3000 | | Serum at 1 in 10000 |
| B | antigen 3 µg/ml | | antigen 3 µg/ml | | antigen 3 µg/ml | | antigen 3 µg/ml | | antigen 3 µg/ml | | antigen 3 µg/ml |
| | Serum at 1 in 30 | | Serum at 1 in 100 | | Serum at 1 in 300 | | Serum at 1 in 1000 | | Serum at 1 in 3000 | | Serum at 1 in 10000 |

TABLE 1-continued

Standard Plate Layouts

| | 1 | 2 | 3 | 4 | 5 | 6 | 7 | 8 | 9 | 10 | 11 | 12 |
|---|---|---|---|---|---|---|---|---|---|---|---|---|
| C | antigen 1 µg/ml Serum at 1 in 30 | | antigen µg/ml Serum at 1 in 100 | | antigen 1 µg/ml Serum at 1 in 300 | | antigen 1 µg/ml Serum at 1 in 1000 | | antigen 1 µg/ml Serum at 1 in 3000 | | antigen 1 µg/ml Serum at 1 in 10000 | |
| D | antigen 0.3 µg/ml Serum at 1 in 30 | | antigen 0.3 µg/ml Serum at 1 in 100 | | antigen 0.03 µg/ml Serum at 1 in 300 | | antigen 0.03 µg/ml Serum at 1 in 1000 | | antigen 0.03 µg/ml Serum at 1 in 3000 | | antigen 0.03 µg/ml Serum at 1 in 10000 | |
| E | antigen 0.1 µg/ml Serum at 1 in 30 | | antigen 0.1 µg/ml Serum at 1 in 100 | | antigen 0.1 µg/ml Serum at 1 in 300 | | antigen 0.1 µg/ml Serum at 1 in 1000 | | antigen 0.1 µg/ml Serum at 1 in 3000 | | antigen 0.1 µg/ml Serum at 1 in 10000 | |
| F | antigen 0.03 µg/ml Serum at 1 in 30 | | antigen 0.03 µg/ml Serum at 1 in 100 | | antigen 0.03 µg/ml Serum at 1 in 300 | | antigen 0.03 µg/ml Serum at 1 in 1000 | | antigen 0.03 µg/ml Serum at 1 in 3000 | | antigen 0.03 µg/ml Serum at 1 in 10000 | |
| G | antigen 0.01 µg/ml Serum at 1 in 30 | | antigen 0.01 µg/ml Serum at 1 in 100 | | antigen 0.01 µg/ml Serum at 1 in 300 | | antigen 0.01 µg/ml Serum at 1 in 1000 | | antigen 0.01 µg/ml Serum at 1 in 3000 | | antigen 0.01 µg/ml Serum at 1 in 10000 | |
| H | carbonate buffer | | carbonate buffer | | carbonate buffer | | carbonate buffer | | carbonate buffer | | carbonate buffer | |

Antigen titration curves were constructed using mean values of duplicates for each sample across the range of serum dilutions. A value corresponding to the level of non-specific binding for each serum dilution was calculated by subtracting a background level (serum at 1/10,000 and no antigen) from the value obtained for binding to no antigen for each serum dilution. This was then used to correct for non-specific binding in each set of duplicates.

Example 2

Detection of Autoantibodies in Primary Breast Cancer

The following data were obtained from a pilot study to assess the sensitivity and reproducibility of a panel of cross titration autoantibody assays (OSAAC) in primary breast cancer (PBC). The study included serum from 14 women with no evidence of cancer and pre-operative serum samples from 14 women with primary breast cancer. Normal and cancer samples were age matched.

The assay was carried out according to the protocol given in example 1 using the antigens p53 and c-myc. Two normal samples (one for p53) had to be removed from the study because they demonstrated sustained and extremely high levels of autoantibody binding across a range of serum and antigen concentrations.

Figure 1B:
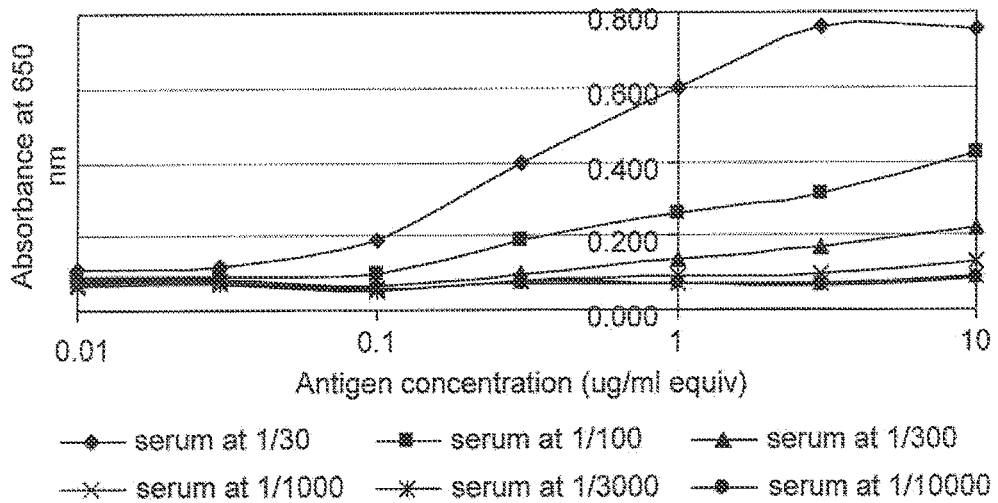
Figure 1C:
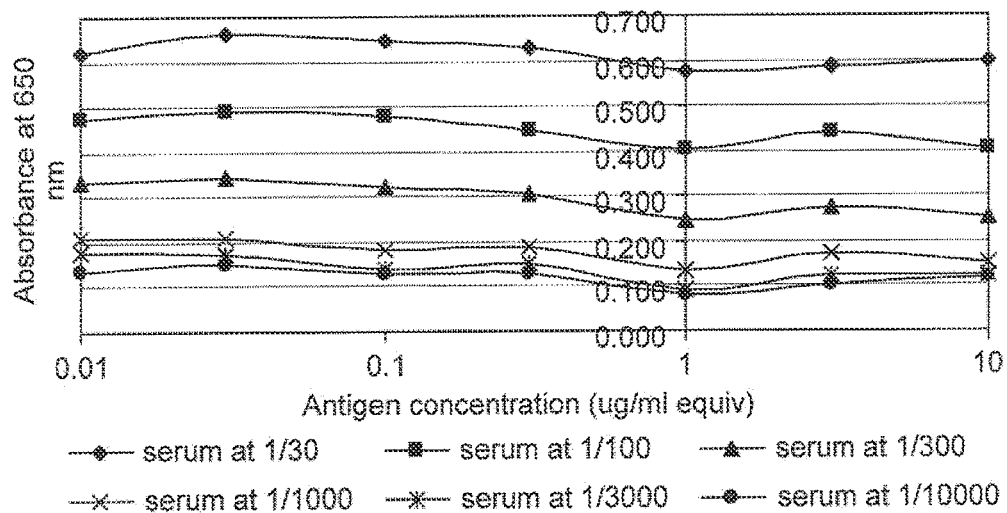
Figure 1D:
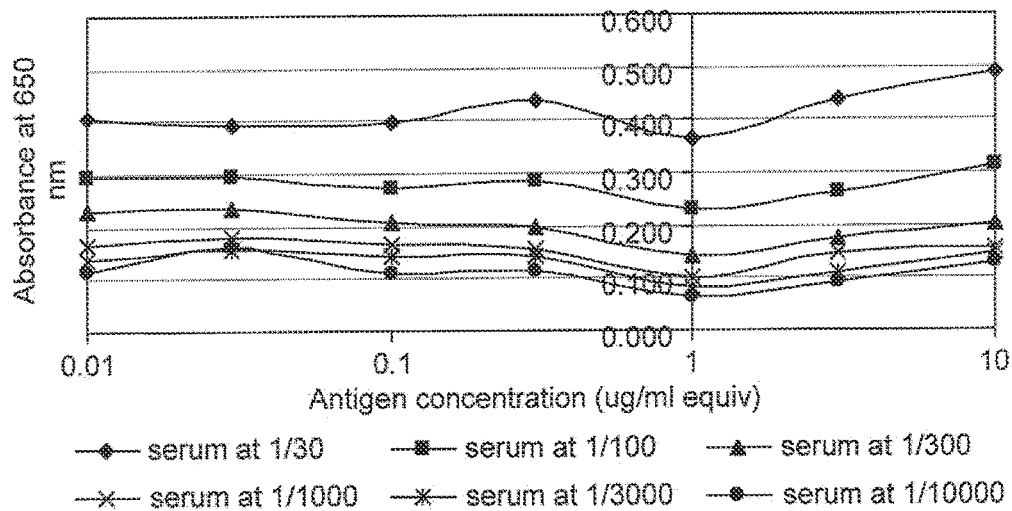
Figure 1E:
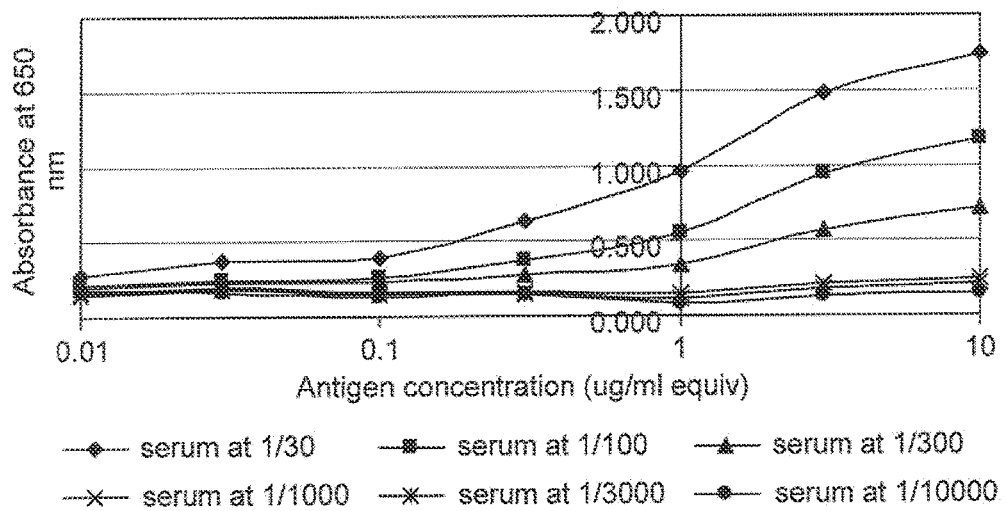
Figure 1F:
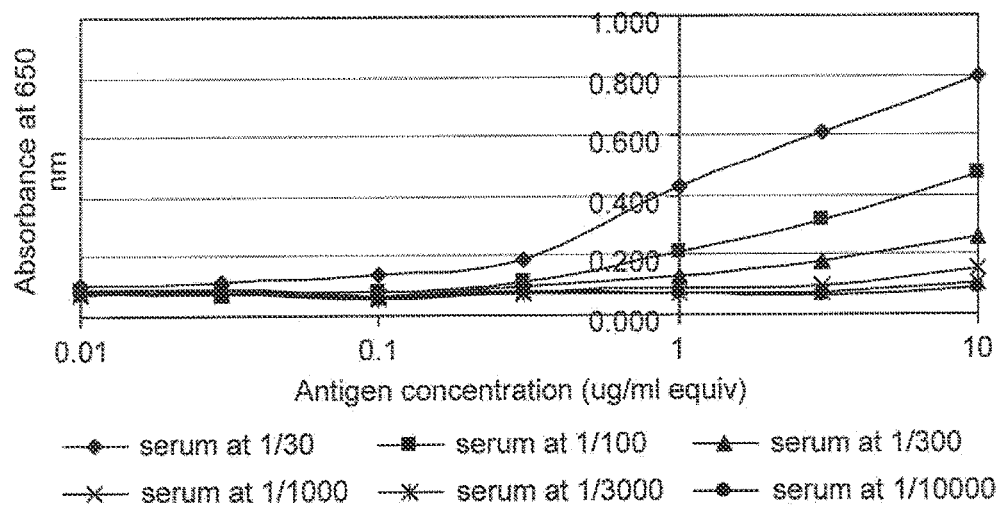
Figure 1G:
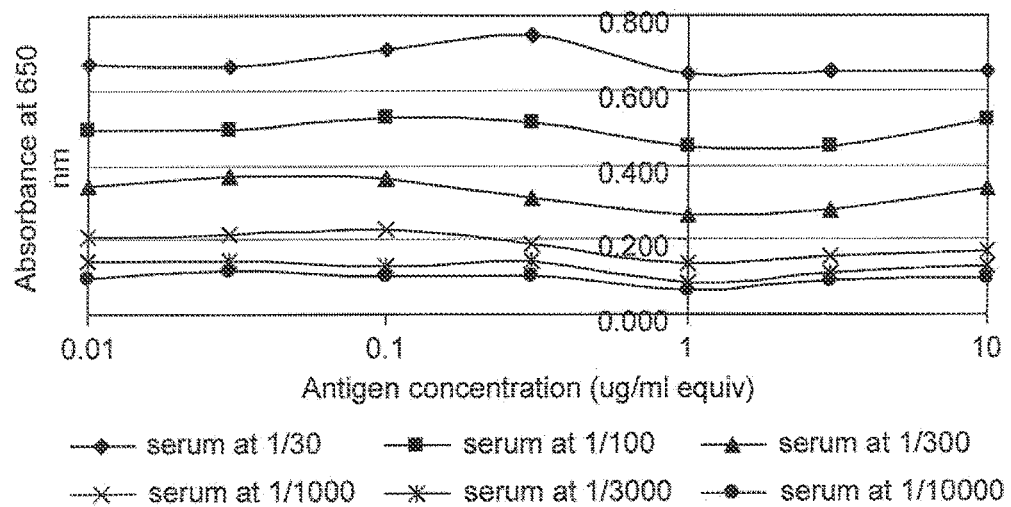
Figure 1H:
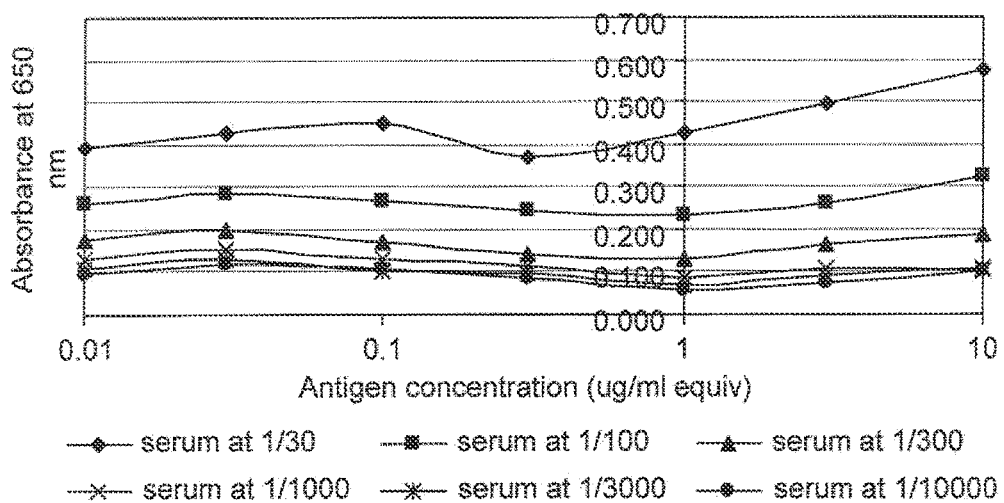

FIG. 1 gives examples of curves obtained when the cross titration assay was used to measure p53 and c-myc autoantibodies in serum. It can be seen that for some samples (e.g. samples 17179 and 18781), a range of titrations were obtained with the most concentrated sera giving the strongest signals as expected. However in other samples (e.g. samples 19150 and 18057), the curves were essentially flat but with increasing signal as the serum concentration increased. This was deemed to be due to non-specific binding of serum immunoglubulins and was compensated for by the non-specific binding correction as described above.

Autoantibody levels were expressed as the optical density (650 nm) due to binding to the test antigen minus that due to non-specific binding. The normal cut-off was calculated as the 95th percentile (mean+2 standard deviations) of the normal group. Samples were deemed to be positive if they showed levels above cut-off in at least 2 serum dilutions between 1/30 and 1/1000 and 2 antigen concentrations between 10 µg/ml and 1 µg/ml. The positive samples are identified in Table 2.

TABLE 2

| | Positive serum samples | | |
|---|---|---|---|
| Antigen | Normal | PBC | |
| P53 | J001 | 17179 | 18781 |
| | | 18237 | 19502 |
| | | 18927 | 19622 |
| | | p53 +ve pool | |
| Total | 1/14 (7%) | 7/14 (50%) | |
| c-myc | J001 | 17179 | 18781 |
| | J041 | 18237 | 18964 |
| | | p53 +ve pool | |
| Total | 2/14 (14%) | 5/14 (36%) | |

Table 2: Positivity of AAb measurements in normal and breast cancer sera. A sample was judged to be positive if the non-specific binding corrected value was higher than the mean+2SD of the normal samples tested in at least two antigen concentrations and two serum dilutions.

Example 3

Analysis of the Sensitivity and Specificity of Cross Titration Assays Compared with Antigen Titration Alone Autoantibody (AAb) measurements were performed on 14 women with primary breast cancer (PBC) using both a cross titration assay (OSAAC) and an antigen only titration method in which autoantibody measurements were only performed at a serum dilution of 1/100. Samples were deemed to be positive if they exceeded cut-off levels at both 10 and 3 µg/ml on an antigen titration curve. Table 2 below shows a direct comparison of the two methods:

TABLE 3

| Antigen | Antigen titration method | | OSAAC Assay | |
|---|---|---|---|---|
| p53 | sensitivity | 5/14 (36%) | 7/14 (50%) | |
| | specificity | 13/14 (93%) | 13/14 (93%) | |
| c-myc | sensitivity | 3/14 (21%) | 5/14 (36%) | |
| | specificity | 12/14 (86%) | 12/14 (86%) | |

Table 3: Comparison of the Antigen Titration method of calculating AAb sensitivities at only one serum dilution compared with OSAAC assay.

It can be seen that by using a series of antigen titration curves in which both antigen concentration and serum concentration are varied, both a higher sensitivity and at least as good specificity were obtained compared with a titration curves in which only antigen concentration is varied.

The cross titration assay (OSAAC) for autoantibody measurement has been shown to be superior to an assay based on antigen titration against a single serum dilution in terms of sensitivity for the detection of primary breast cancer. This is the case for both p53 and c-myc autoantibodies and there is no reason to assume that this will not be true for a range of antigens. Without being bound by theory, the applicant considers there are a number of reasons for the observed higher sensitivity of assays based on cross titration of antigen and test sample.

(i) The assay format has a much broader dynamic range. This provides the scope to detect both low affinity antibodies at high antigen concentrations as well as high abundance antibodies which would otherwise hook at high antigen concentration.
(ii) Low abundance antibodies that may be masked by high levels of non-specific binding can be detected at low serum concentration.
(iii) The stringent criteria for defining a sample as positive (above mean+2SD of a normal population for at least 2 antigen concentrations and 2 serum dilutions) applied here means that the technician can be much more confident that a positive measurement is a true positive.

Example 4

Detection of Primary Breast Cancer Sera by Antigen Cross-Titration

Sera from women with primary breast cancer (PBC, n=8 (6 PBC sera were the same between all antigens and 2 PBC sera were specific to either p53 or the ECD6 proteins)) and women with no evidence of malignant disease (n=10) were used in this study. The assay was performed in duplicate using a modification of the general protocol described in Example 1. Briefly set of microtitre plates were coated with antigen proteins: recombinant p53, ECD6 (also known as the HER2 external domain), or an ECD6 3' fragment. The ECD6 antigen comprises amino acids 1 to 647 of the full length HER2 (erbB-2) amino acid sequence shown under accession NM_004439 fused to an N-terminal biotinylation sequence and a C-terminal His tag. The ECD6 3' fragment antigen comprises amino acids 361 to 647 of the full length HER2 (erbB-2) amino acid sequence shown under accession NM_004439, again fused to an N-terminal biotinylation sequence and a C-terminal His tag.

The antigens were serially titrated down each plate at concentrations (top to bottom) of 160 nM, 50 nM, 16 nM, 5 nM, 1.6 nM, 0.5 nM, 0.16 nM. A "no antigen" control of buffer only was included as the bottom row of each plate. The antigens were allowed to adsorb for 48 hours after which time the plates were washed and blocked for 90 min with PBS containing casein (0.1% w/v) and NaCl (0.5M).

During the blocking incubation a set of serial serum titrations were prepared in tubes, at dilutions of 1:1600, 1:800, 1:400, 1:200, 1:100 and 1:50. Following removal of the blocking buffer, these were added to the antigen-coated plates (dilutions 1:1600, 1:800, 1:400, 1:200, 1:100 and 1:50 added across the plates left-to-right) and incubated for 90 min. The remainder of the assay was performed as described in Example 1. (Plate layout is summarised in FIG. 2)

Antigen titration curves were constructed using mean values of duplicates for each sample across the range of serum dilutions. A value corresponding to the level autoantibody response was achieved by subtracting non-specific background (the serum response against 0.16 nM antigen).

Results

Figure 3A:
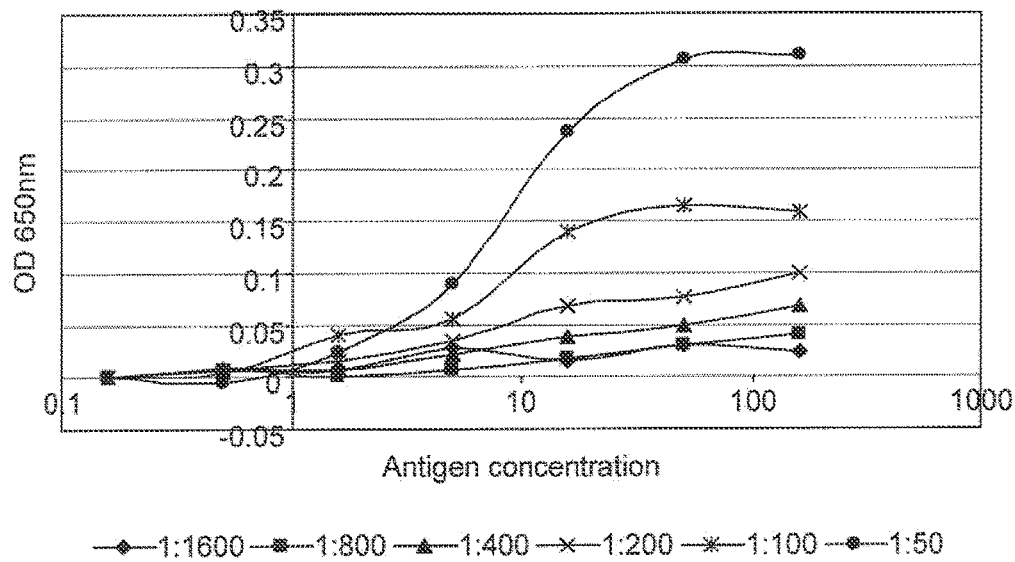
FIGS. 3*a*-3*b*, 4*a*-4*b*, 5*a*-5*b*, 6*a*-6*c*, and 7*a*-7*d* show a series of cross-titration curves for detection of autoantibodies against p53, ECD6 (also known as the extracellular domain of HER2) and a 3' fragment of ECD6 in samples of serum taken from patients with primary breast cancer and normal control subjects. In each experiment, six different dilutions of the patient serum were separately tested for specific binding against a titration series of varying amounts of recombinant p53, ECD6 or ECD6 3' fragment antigens. For each antigen, separate curves of specific binding (expressed as absorbance at 650 nm) versus antigen concentration were plotted for each dilution of the patient serum.
Figure 3B:
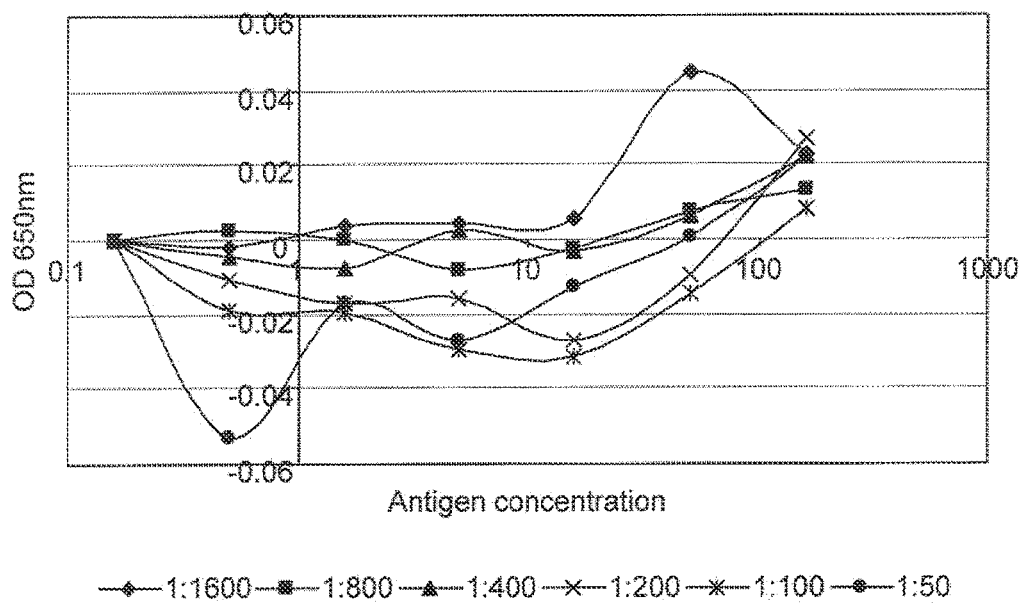
Figure 4A:
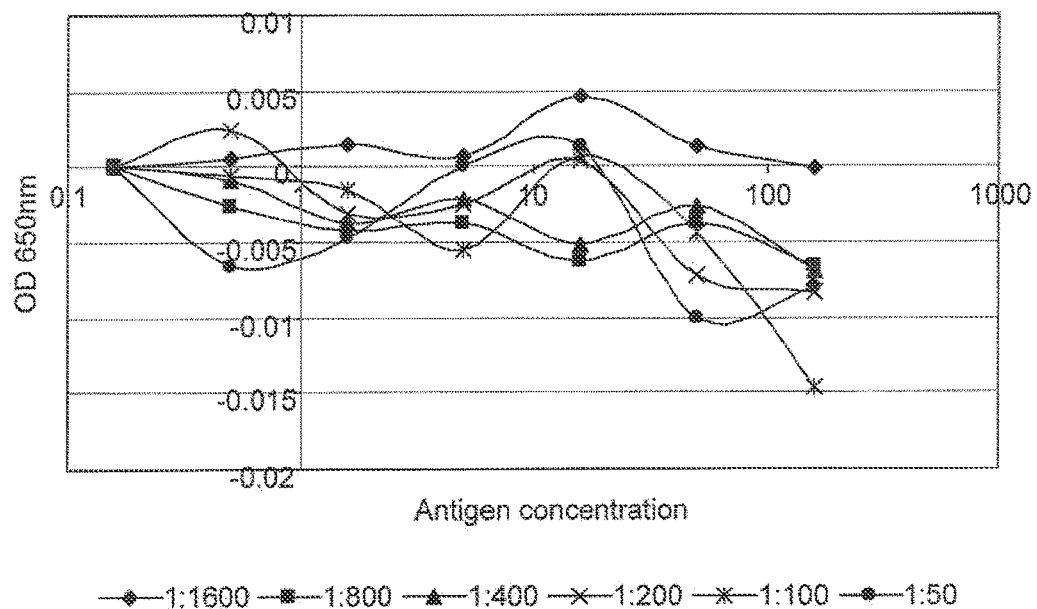
Figure 4B:
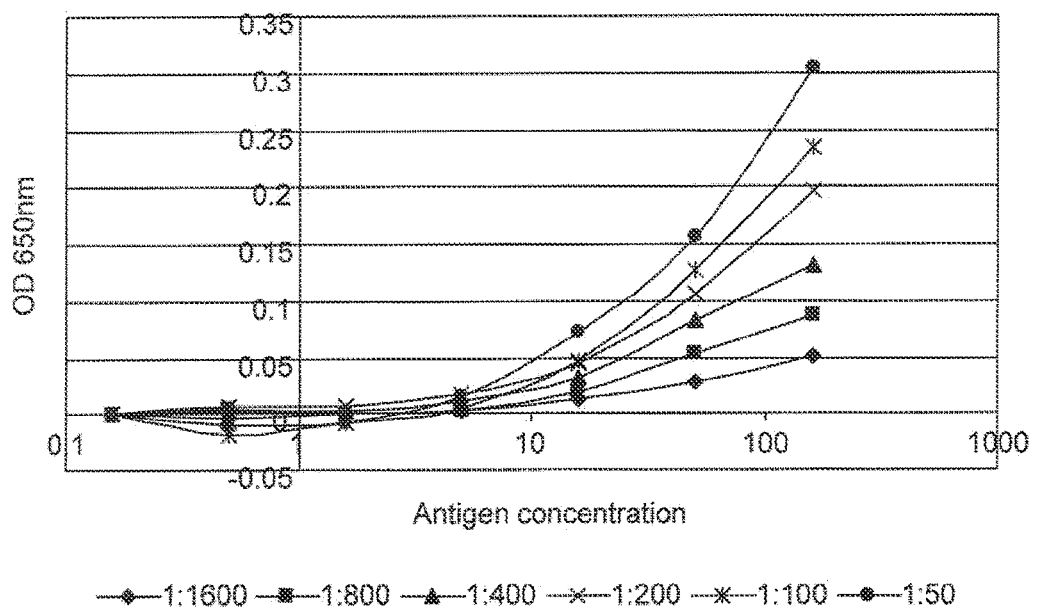
Figure 5A:
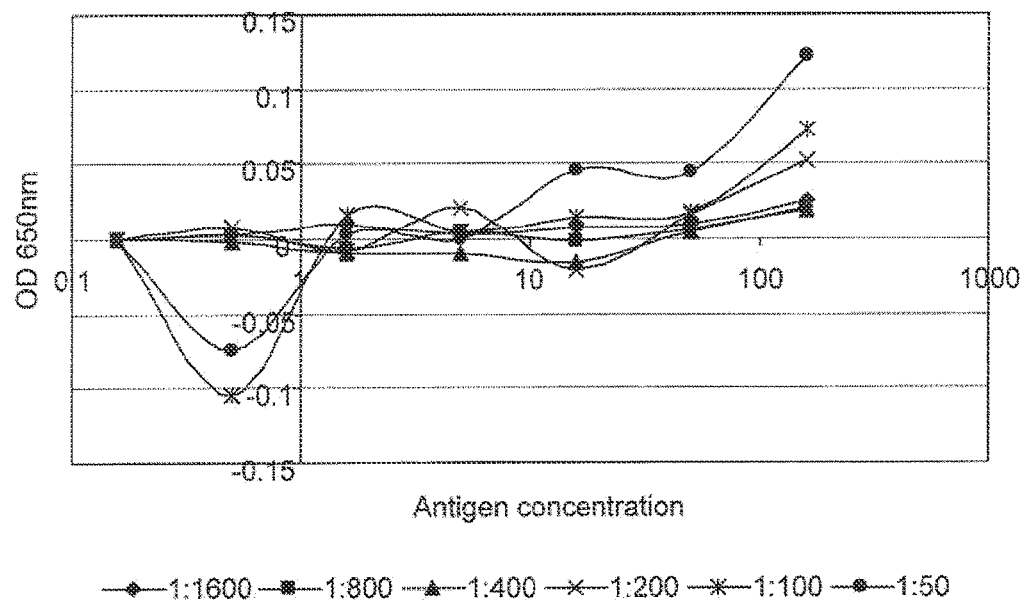
Figure 5B:
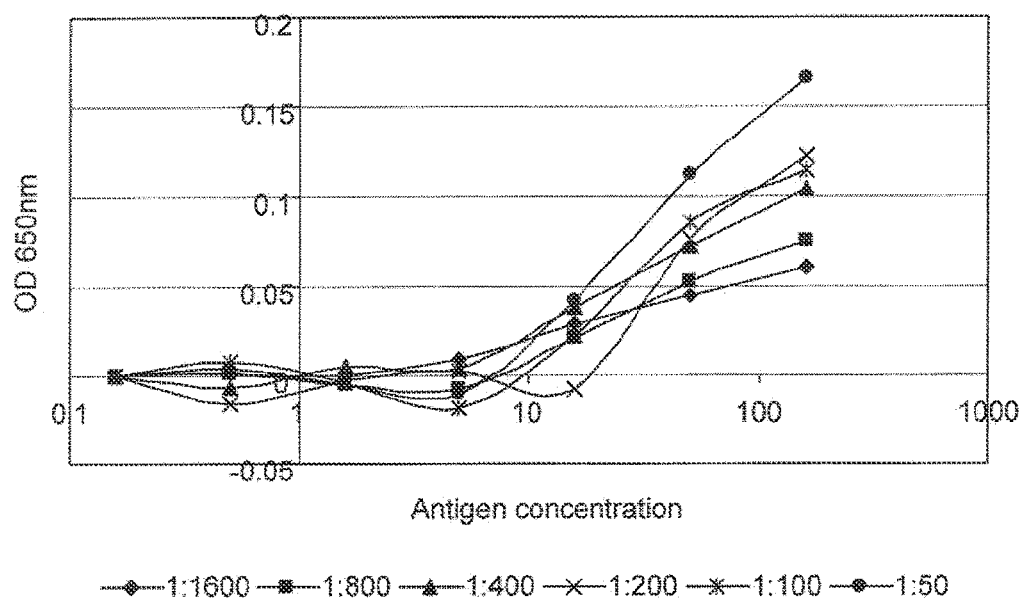
Figure 6A:
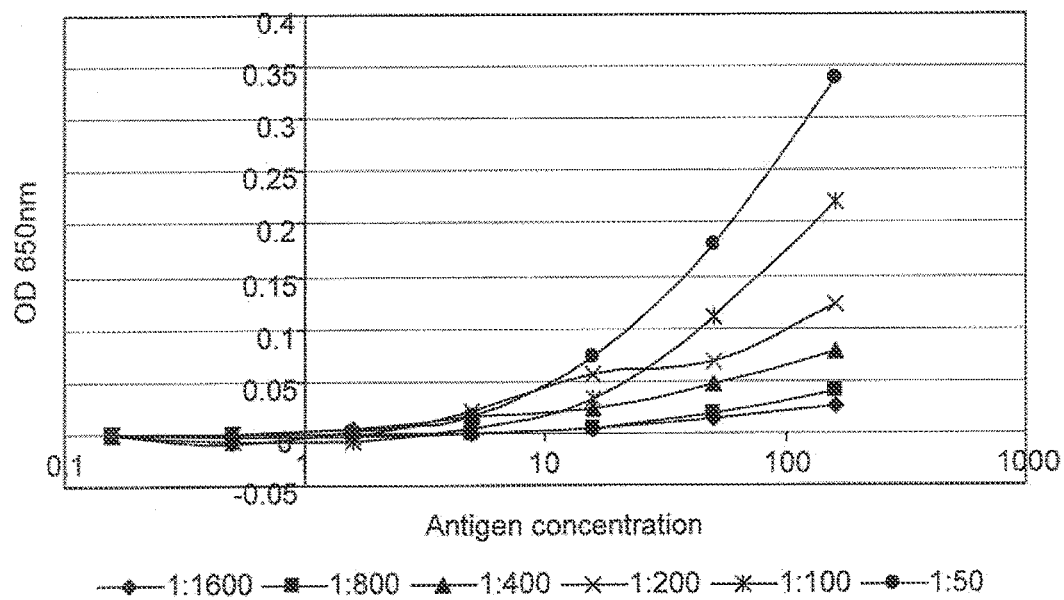
Figure 6B:
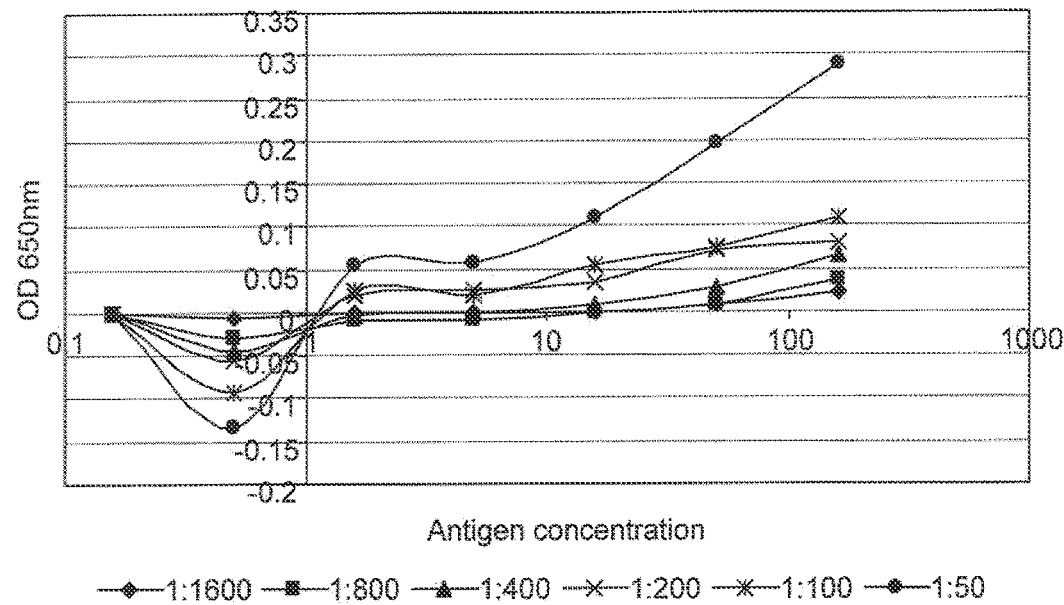
Figure 6C:
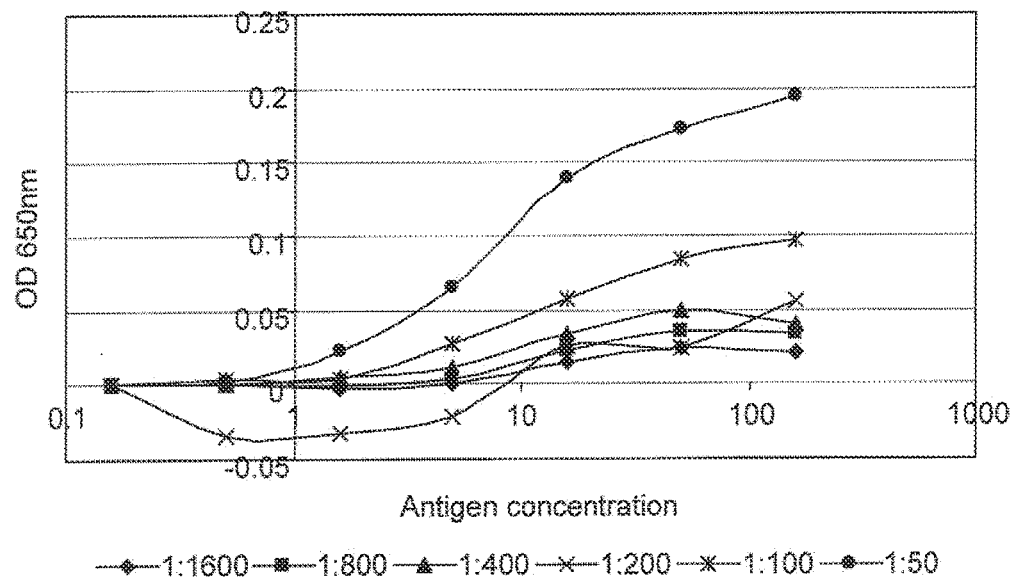
Figure 7A:
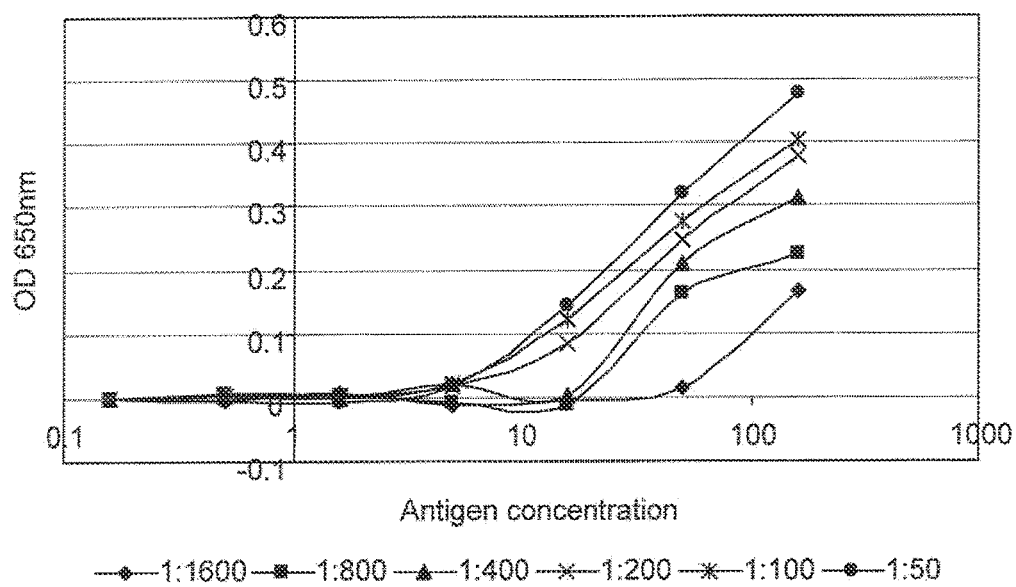
Figure 7B:
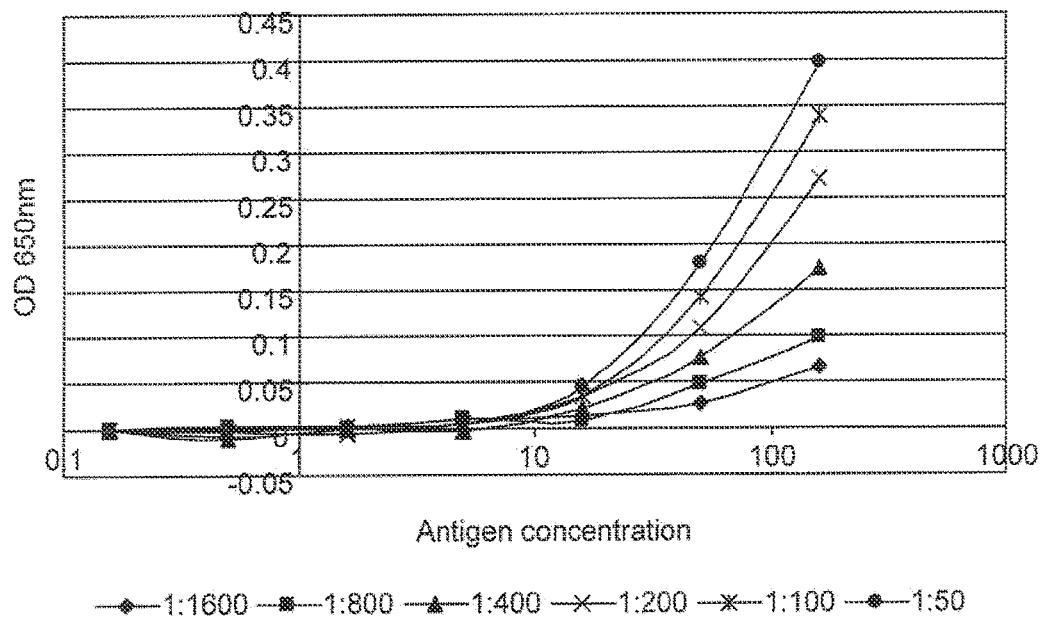
Figure 7C:
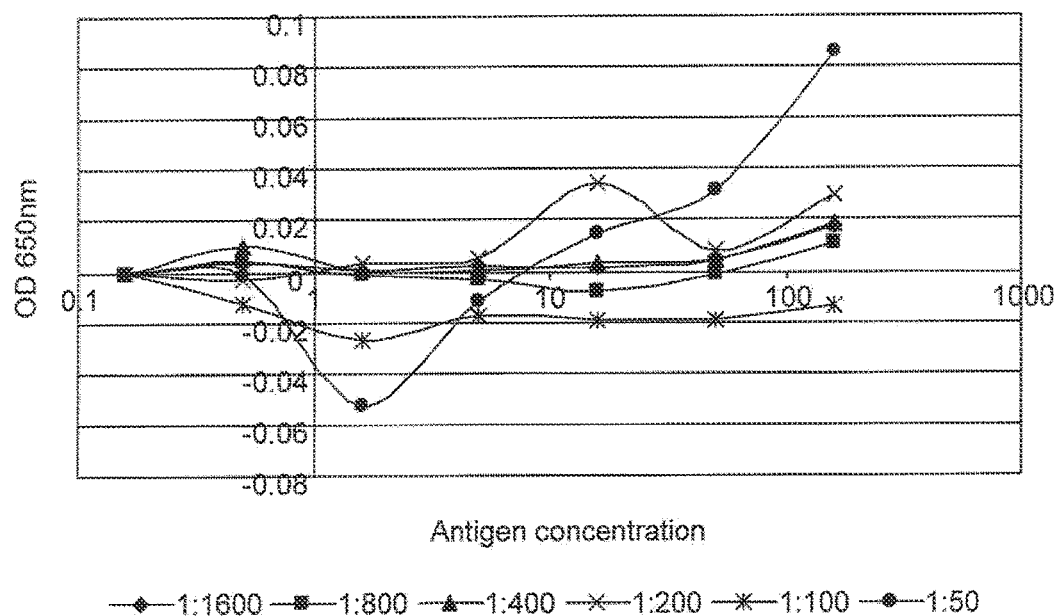
Figure 7D:
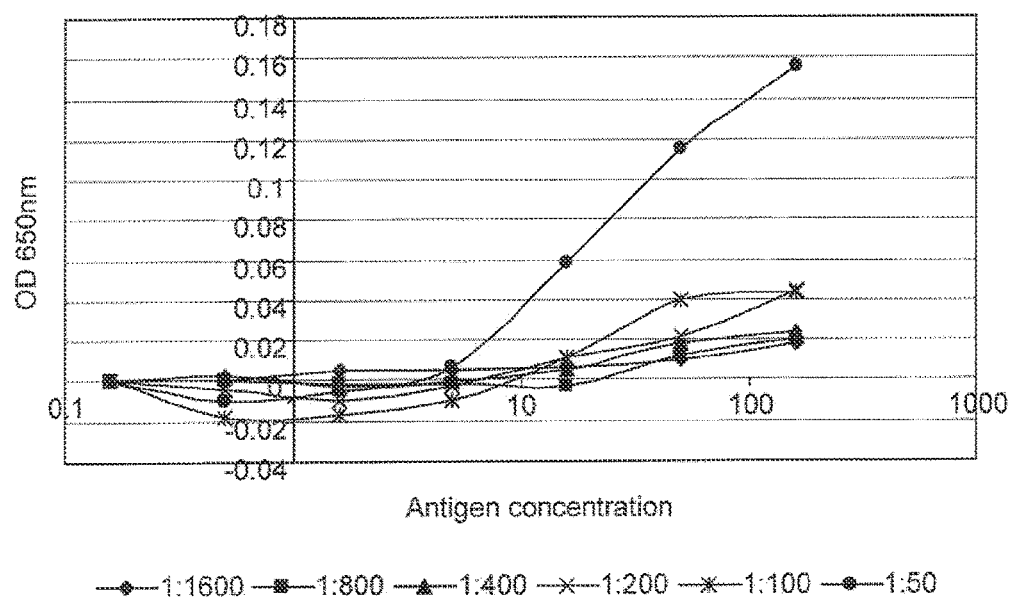

Representative titration curves are shown in FIGS. 3a-3b, 4a-4b, 5a-5b, 6a-6c, and 7a-7d. It can be seen that for some samples (e.g. samples 20642 and 20620 for ECD6), a range of titrations were obtained with the most concentrated sera giving the strongest signals as expected. However in other samples (e.g. samples MVV272 and EAO220 for ECD6 3' fragment), the curves were essentially flat but with increasing signal as the serum concentration increased. This was deemed to be due to non-specific binding of serum immunoglobulins.

Positive cut-offs were calculated as the mean+2SDs of the normal population. Samples were deemed to be positive if they showed levels above cut-off in both runs and at either 160 nM or 50 nM antigen concentrations. Table 4 demonstrates that a serum dilution of 1:100 currently used for autoantibody detection is not always optimal. In addition the table shows that there is inter-antigen variation of the optimal serum dilution. The highest level of sensitivity for ECD6 was 75% when serum was diluted 1:50. This was the opposite for the ECD6 3' fragment where 1:50 had a 0% sensitivity. This was in part due to increased signal against ECD6 3' fragment in the normal samples analysed (e.g. samples MMV272 and EAO220).

TABLE 4

| | Serum Dilution | | | | | |
|---|---|---|---|---|---|---|
| | 1:1600 | 1:800 | 1:400 | 1:200 | 1:100 | 1:50 |
| p53 | 0% | 25% | 37.5% | 37.5% | 37.5% | 37.5% |
| ECD6 | 25% | 37.5% | 50% | 50% | 50% | 75% |
| ECD6 3' | 37.5% | 37.5% | 37.5% | 37.5% | 12.5% | 0% |

Table 4: Sensitivity of the autoantibody assay against the 8 PBC samples analysed for each antigen. A sample was judged to be positive if the non-specific binding corrected value was higher than the mean+2SD of the normal samples tested at either of two antigen concentrations.

Table 5 summarises the specificity of the assay where serum is diluted to different concentrations. No difference in assay specificity was observed using the samples analysed in this assay.

TABLE 5

| | Serum Dilution | | | | | |
|---|---|---|---|---|---|---|
| | 1:1600 | 1:800 | 1:400 | 1:200 | 1:100 | 1:50 |
| p53 | 100% | 100% | 100% | 100% | 100% | 100% |
| ECD6 | 100% | 100% | 100% | 100% | 100% | 100% |
| ECD6 3' | 100% | 100% | 100% | 100% | 100% | 100% |

Table 5: Specificity of the autoantibody assay with the 10 PBC samples. A sample was judged to be positive if the non-specific binding corrected value was higher than the mean+2SD of the normal samples tested at either of two antigen concentrations.

In Table 6 the optimum serum dilution is compared for the 6 PBC sera that were analysed against all antigens. The optimum serum dilution is the highest dilution where an autoantibody response can be detected. By way of example, serum 20628 could be diluted to 1:800 and a response (i.e. autoantibodies) against p53 could be detected but the same serum needed to be diluted 1:50 for detection of autoantibodies to ECD6. The optimal dilution for this antigen would therefore be 1:50 so that all positive autoantibody responses could be identified.

TABLE 6

| Optimum Dilution per Antigen | | | | |
|---|---|---|---|---|
| Serum | P53 | ECS6 | ECD6 3' | Optimum Dilution |
| 20593 | — | — | — | — |
| 20641 | — | 1:50 | — | 1:50 |
| 20620 | — | 1:1600 | 1:1600 | 1-1600 |
| 20637 | — | — | — | — |
| 20628 | 1:800 | 1:50 | — | 1:50 |
| 20642 | 1:400 | 1:400 | — | 1:400 |

Table 6: Optimal inter-individual dilution of the 6 PBC serum samples that were analysed against all antigens. Where the lowest dilution is displayed that was required to detect an autoantibody response against either P53, ECD6 or ECD6 3' fragment.

Table 7 summarises the increased overall assay sensitivity for detection of primary breast cancer when using the cross titration method to detect autoantibodies against each of the tested antigens.

TABLE 7

| | Cross Titration | Serum at 1:100 |
|---|---|---|
| Sensitivity | 66.7% | 33.3% |
| Specificity | 100% | 100% |

Table 7: Overall assay sensitivity and specificity using both ECD6 and ECD6 3' fragment if the cross titration assay is used instead of serum diluted at 1:100 for the 6 PBC serum samples analysed against all antigens.

Conclusions

The OSAAC assay for autoantibody measurement has been shown to be superior to antigen titration alone in terms of sensitivity for the detection of primary breast cancer. This is the case for p53, ECD6 and ECD6 3' autoantibodies and there is no reason to assume that this will not be true for all tumour marker autoantibodies. It would appear that this is due to the fact that this assay format has a much broader dynamic range. This provides the scope to detect both low affinity autoantibodies at high antigen concentrations as well as high abundance autoantibodies which would otherwise hook at high antigen concentration. In addition it appears possible that low abundance autoantibodies that may be masked by high levels of non-specific binding can be detected at low serum concentration.

All patents, patent applications, and published references cited herein are hereby incorporated by reference in their entirety. While this invention has been particularly shown and described with references to preferred embodiments, it will be understood by those skilled in the art that various changes in form and details may be made without departing from the scope of the invention encompassed by the claims.

We claim:

1. A method of predicting response to anti-cancer treatment, the method comprising detecting an autoantibody in a test sample, wherein the test sample comprises a bodily fluid from a human patient, and wherein comparison of a level of autoantibody in the patient with a previously established relationship between level of autoantibody and likely outcome of treatment is used to predict whether the patient will respond to the anti-cancer treatment, which method comprises, (a) preparing two or more different dilutions of the test sample and carrying out the following steps (i) and (ii) in respect of each test sample dilution in order to provide a cross-titration assay based on testing two or more dilutions of a test sample against two or more dilution of antigen to form a titration curve:
  (i) contacting each of the two or more test sample dilution with two or more different amounts of an antigen specific for the autoantibody,
  (ii) detecting the amount of specific binding between the autoantibody and the antigen for each amount of antigen used in step (i),
(b) plotting or calculating a separate curve of the amount of specific binding versus the amount of antigen for each of the two or more test sample dilutions used in step (a),
(c) determining the progress of cancer or recurrence of cancer based upon the amount of specific binding between the autoantibody and the antigen for each test sample dilution at each amount of antigen tested,
wherein a change in the amount of specific binding, when compared to controls, predicts that the patient will respond to the anti-cancer treatment.

2. The method of claim 1 wherein the anti-cancer treatment is vaccination, anti-growth factor or signal transduction therapy, radiotherapy, endocrine therapy, human antibody therapy or chemotherapy.

3. The method of claim 1 wherein the presence in the test sample of autoantibody reactive with the antigen used in the assay is indicated by a generally S shaped or sigmoid curve for at least two different dilutions of the test sample.

4. A method of monitoring the response of a human cancer patient to anti-cancer treatment, the method comprising detecting an autoantibody in a test sample, wherein the sample to be tested using the method is a sample of bodily fluid taken from the patient, and wherein a change in the level of autoantibodies after treatment is taken as an indication of whether or not the patient has responded to the treatment, which method comprises, (a) preparing two or more different dilutions of the test sample and carrying out the following steps (i) and (ii) in respect of each test sample dilution:
  (i) contacting the test sample dilution with a plurality of different amounts of an antigen specific for the autoantibody,
  (ii) detecting the amount of specific binding between the autoantibody and the antigen for each amount of antigen used in step (i),
(b) plotting or calculating a separate curve of the amount of specific binding versus the amount of antigen for each test sample dilution used in step (a),
(c) determining the progress of cancer or recurrence of cancer based upon the amount of specific binding between the autoantibody and the antigen for each test sample dilution and amount of antigen tested,
wherein a change in the level of autoantibodies after treatment is taken as an indication that the patient has responded positively to the treatment.

5. The method of claim 4 wherein the treatment is vaccination, anti-growth factor or signal transduction therapy, radiotherapy, endocrine therapy, human antibody therapy or chemotherapy.

* * * * *